United States Patent [19]

Tóth et al.

[11] Patent Number: 5,157,038
[45] Date of Patent: Oct. 20, 1992

[54] 2-OXO-1-OXA-8 AZASPIRO[4,5]DECANE DERIVATIVES, PHARMACEUTICAL COMPOSITIONS CONTAINING THEM AND PROCESS FOR PREPARING SAME

[75] Inventors: Edit Tóth; József Törley; Béla Hegedüs; László Szporny; Béla Kiss; Éva Pálosi; Dóra Groó; István Laszlovszky; Erzsébet Lapis; Ferenc Auth; László Gaál, all of Budapest, Hungary

[73] Assignee: Richter Gedeon Vegyeszeti Gyar Rt., Budapest, Hungary

[21] Appl. No.: 566,274

[22] Filed: Aug. 10, 1990

[30] Foreign Application Priority Data

Aug. 10, 1989 [HU] Hungary .............. 4092/89

[51] Int. Cl.⁵ .................. A61K 31/445; C07D 491/10
[52] U.S. Cl. ..................... 514/278; 514/236.8; 514/255; 544/70; 544/230; 546/19
[58] Field of Search .............. 546/19; 514/278, 236.8, 514/255; 544/70, 230

[56] References Cited

U.S. PATENT DOCUMENTS

| | | | |
|---|---|---|---|
| 3,399,192 | 8/1968 | Regnier | 544/230 |
| 3,594,386 | 7/1971 | Regnier et al. | 514/929 |
| 3,655,673 | 4/1972 | Maillard | 546/19 |
| 3,856,797 | 12/1974 | Arimura | 544/70 |

FOREIGN PATENT DOCUMENTS 1301254 12/1972 United Kingdom .............. 546/19

*Primary Examiner*—Jane T. Fan
*Assistant Examiner*—Celia Chang

*Attorney, Agent, or Firm*—Herbert Dubno; Jonathan Myers

[57] ABSTRACT

The invention relates to novel 2-oxo-1-oxa-8-azaspiro[4,5]decane derivatives of the formula (I),

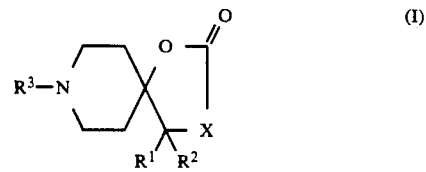

wherein
X means oxygen or an >NR group, wherein
R stands for hydrogen; a $C_{1-12}$alkyl; $C_{3-6}$cycloalkyl; carbocyclic $C_{6-10}$aryl or carbocyclic $C_{6-10}$aryl-$C_{1-4}$alkyl group, the two latter two substituents optionally substituted on their aromatic moiety by one or more, same or different halogen, one or more $C_{1-4}$alkyl, $C_{1-4}$alkoxy or trihalomethyl group; or a tosyl group;
$R^1$ and $R^2$ together represent a methylene group or, when X stands for an >NR group wherein R is as defined above, one of $R^1$ and $R^2$ m may represent a hydroxyl group and the other one is a methyl group; and
$R^3$ means hydrogen, benzyl, ($C_{1-4}$alkoxy)carbonyl, phenoxycarbonyl, benzyloxycarbonyl, formyl, piperidin-1-ylcarbonyl, morpholin-4-ylcarbonyl, 4-methylpiperazin-1-ylcarbonyl, 4-(2-hydroxyethyl)piperazin-1-ylcarbonyl, 2-chloro-3-nicotinoylcarbamoyl or $C_{1-6}$alkylcarbamoyl group, as well as their acid addition and quaternary ammonium salts.

4 Claims, No Drawings

2-OXO-1-OXA-8 AZASPIRO[4,5]DECANE DERIVATIVES, PHARMACEUTICAL COMPOSITIONS CONTAINING THEM AND PROCESS FOR PREPARING SAME

The invention relates to novel, therapeutically active 2-oxo-1-oxa-8-azaspiro[4,5] decane derivatives of the formula (I),

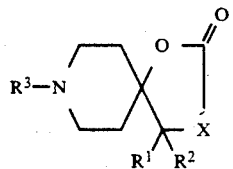

wherein
- X means oxygen or an >NR group, wherein
  R stands for hydrogen; a $C_{1-12}$alkyl; $C_{3-6}$cycloalkyl; carbocyclic $C_{6-10}$aryl or carbocyclic $C_{6-10}$aryl-$C_{1-4}$alkyl group, the two latter substituents are optionally substituted on their aromatic moiety by one or more, same or different halogen, one or more $C_{1-4}$alkyl, $C_{1-4}$alkoxy or trihalomethyl group(s); or a tosyl group;
- $R^1$ and $R^2$ together represent a methylene group or, when X stands for an >NR group where in R is as defined above, one of $R^1$ and $R^2$ may represent a hydroxyl group and the other one is a methyl group; and
- $R^3$ means hydrogen, benzyl, ($C_{1-4}$alkoxy)carbonyl, phenoxycarbonyl, benzyloxycarbonyl, formyl, piperidin-1-ylcarbonyl, morpholin-4-ylcarbonyl, 4-methylpiperazin-1-ylcarbonyl, 4-(2-hydroxyethyl)piperazin-1-ylcarbonyl, 2-chloro-3-nicotinoylcarbamoyl or $C_{1-6}$alkylcarbamoyl group, as well as their acid addition and quaternary ammonium salts and pharmaceutical compositions containing these compounds.

The invention also relates to a process for the preparation of the above compounds and compositions as well as to a method of treatment. The latter comprises administering a therapeutically effective amount of a compound of formula (I) or a pharmaceutically acceptable acid addition or quaternary ammonium salt thereof into the organism of a patient.

The compounds of the formula (I) may contain one or more asymmetric carbon atom(s) and consequently, then may exist in various stereoisomeric forms. Furthermore, the compounds of the formula (I) may be in the form of bases, acid addition or quaternary ammonium salts, racemates, individual optical isomers and their mixtures, all of which may occur in the form of various solvates such as hydrates. All there compounds and mixtures are within the scope of the invention.

A number of therapeutically useful 2-oxo-1-oxa-3,8-diazaspiro [4,5] decane derivatives have been described in the literature. Such compounds are reported e.g. in the following publications: CA. 71, 91339d (1969); C.A. 78, 719668t (1973); C.A. 78, 23876q (1973); C.A. 81, 33153a and 105368b (1974); C.A. 95, 161765e (1981); as well as in the DE patent specifications Nos. 2,013,729, 2,013,668 and 2,163,000; in the BE patent specifications Nos. 775,894, 774,170, 786,631 and 825,444; in the GB patent specification No. 1,100,281; in the published NL patent application No. 7,214,689 as well as in the U.S. Pat. Nos. 3,555,053, 3,594,386, 4,244,961 and 4,255,432.

A substantial difference between the compounds of formula (I) according to the invention and similar derivatives known up to the present appears in the nature of the substituents bound in position 4 and optionally in position 3 of the spirodecane skeleton.

According to an other aspect of the invention there is provided a process for the preparation of compounds of the formula (I) as well as their acid addition and quaternary ammonium salts, which comprises a) reacting a 4-ethynyl-4-hydroxypiperidine derivative of the formula (III),

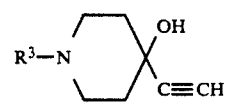

wherein $R^3$ is as defined above, with an isocyanate of the formula R-NCO, wherein R is as defined above, and then cyclizing the obtained 4-carbamoyloxy-4-ethynyl-piperidine derivative of formula (II),

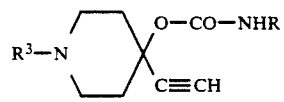

wherein R and $R^3$ are as defined above,

α) in an acidic medium and reacting the obtained salt of a 2-imino-1,3-dioxolane derivative of the formula (VI),

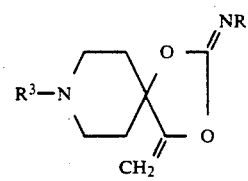

wherein R and $R^3$ are as defined above, with water to obtain compounds of the formula (I), wherein X means oxygen, $R^1$ and $R^2$ together represent a methylene group, and $R^3$ is as defined above; or β) in a basic medium to obtain compounds of the formula (I), wherein X means an >NR group, $R^1$ and $R^2$ together represent a methylene group, and R as well as $R^2$ are as defined above; or b) cyclizing in an acid medium a 4-carbamoyloxy-4-ethynylpiperidine derivative of the formula (II), wherein R and $R^3$ are as defined above, and reacting the obtained salt of a 2-imino-1,3-dioxolane derivative of the formula (VI), wherein R and $R^3$ are as defined above, with water to obtain compounds of the formula (I), wherein X means oxygen, $R^3$ is as defined above and $R^1$ together with $R^2$ represents a methylene group; or c) cyclizing a 4-carbamoyloxy-4-ethynylpiperidine derivative of formula (II) wherein R and $R^3$ are as defined above, in a basic medium to obtain compounds of the formula (I), wherein X means an >NR group, $R^1$ together with $R^2$ represents a methylene group and R as well as $R^3$ are as defined above; or d) reacting a 4-acetyl-4-hydroxypiperidine derivative of the formula (IV),

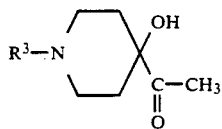

wherein $R^3$ is as defined above, with an isocyanate of the formula R-NCO, wherein R is as defined above, and cyclizing the thus formed 4-acetyl-4-carbamoyloxypiperidine derivative of formula (V),

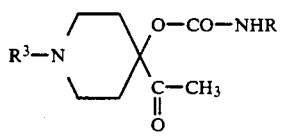

wherein R and $R^3$ are as defined above, to obtain compounds of the formula (I), wherein X means an >NR group, one of $R^1$ and $R^2$ stands for a hydroxyl group and the other is a methyl group, and R as well as $R^3$ are as defined above; or e) cyclizing a 4-acetyl-4-carbamoyloxypiperidine derivative of the formula (V), wherein R and $R^3$ are as defined above, to obtain compounds of the formula (I), wherein X means and >NR group, one of $R^1$ and $R^2$ stands for a hydroxyl group and the other is a methyl group, and R as well as $R^3$ are as defined above, then, if desired, reacting a thus prepared compound of the formula (I), wherein X means oxygen, $R^3$ is as defined above and $R^1$ together with $R^2$ represents a methylene group, with an amine of the formula $R-NH_2$, wherein R is as defined above, to obtain compounds of the formula (I), wherein X means an >NR group, one of $R^1$ and $R^2$ stands for a hydroxyl group and the other is a methyl group, and R as well as $R^3$ are as defined above; and/or transforming a thus prepared compound of the formula (I), wherein X, R, $R^1$, $R^2$ and $R^3$ are as defined above, to an other compound of the formula (I) falling within the scope of the formula (I); and/or reacting a thus prepared compound of the formula (I), wherein X, R, $R^1$, $R^2$ and $R^3$ are as defined above, with an acid to give an acid addition salt and/or treating a compound of the formula (I), wherein X, R, $R^1$, $R^2$ and $R^3$ are as defined above, obtained as a salt, with a base to liberate the base form thereof and/or converting a thus prepared compound of the formula (I), wherein X, R, $R^1$, $R^2$ and $R^3$ are as defined above, to its quaternary ammonium salt.

In the first step of process a) according to the invention a 4-ethynyl-4-hydroxypiperidine derivative of the formula (III) is brought into reaction with an isocyanate of the formula R-NCO in a manner known per se [Houben-Weyl: Methoden der Organischen Chemie Vol. VIII/3, pages 137 to 147 (1952)] to give a 4-carbamoyloxy-4-ethylonylpiperidine derivative of the formula (III), which is cyclized in an acidic medium according to step α) or in a basic medium according to step β).

According to step α), the obtained 4-carbamoyloxy-4-ethynylpiperidine derivative of formula (II) is cyclized in an acidic medium and then the thus formed salt of a 2-imino-1,3-dioxolane derivative of formula (VI) is reacted with water. The cyclization is carried out in an inert organic solvent (i.e. in a solvent which is insert under the reaction conditions), in the presence of a suitable acid, preferably in the presence of a dry halogen halide. Aliphatic or alicyclic ethers such as diethyl ether, dipropyl ether, diisopropyl ether, dibutyl ether, tetrahydrofuran or dioxane as well as lower aliphatic carboxylic acids, e.g. acetic or propionic acid, may be employed as solvents.

As a hydrogen halide hydrogen chloride, bromide, iodide or fluoride, preferably hydrogen chloride or bromide are used. After treating with water the thus formed 2imino-1,3-dioxalane hydrohalide salt, the 2-oxo-1-oxa-8-azaspiro[4,5]decane derivative of the formula (I) is obtained as an acid addition salt, from which, if desired, the base can be liberated in a manner known per se.

The cyclization of the obtained 4-carbamoyloxy-4-ethynylpiperidine derivative of formula (II) according to the step β) is realized in the presence of a base. Alkaline metal acetates, carbonates, alkoxides, hydroxides and/or tertiary organic bases, e.g. pyridine, tripropylamine or picoline, may be used as basic catalyst in the cyclization; the organic bases may also serve as solvents for the reaction. Further suitable solvents are aliphatic alcohols, e.g. methanol, ethanol, propanol or butanol; aliphatic, alicyclic or aromatic hydrocarbons, e.g. hexane, cyclohexane, benzene, toluene or xylene; acid amides, e.g. dimethyl formamide or N-methyl-2-pyrrolidone; ethers such as dibutyl ether or dioxane; nitriles such as acetonitrile; sulfoxides, e.g. dimethyl sulfoxide, etc.; as well as the mixtures of the above solvents. The reaction may be carried out without any solvent, too, e.g. in a molten state. In order to accelerate the cyclization the temperature is suitably increased; the reaction is preferably accomplished between 40° C. and the boiling point of the reaction mixture. It is suitable to work under an inert gas such as argon or nitrogen. According to a preferred embodiment, when $R^3$ is different from 4-(2-hydroxyethyl)piperazin-1-ylcarbonyl) or 2-chloro-3-nicotinoylcarbamoyl group, the 4-carbamoyloxy-4-ethynylpiperidine derivative of the formula (II) resulting from the reaction of a 4-ethynyl-4-hydroxypiperidine derivative of the formula (III) with an isocyanate of formula R-NCO is not isolated but directly cyclized in the same reaction mixture in the presence of a suitable base.

In the processes b) and c) of the invention the procedures discussed under steps α) and β) are followed.

In the process d) of the invention as 4-acetyl-4-hydroxypiperidine derivative of the formula (IV) is reacted with an isocyanate of the formula R-NCO and the obtained 4-acetyl-4-carbamoyloxypiperidine derivative of the formula (V) is cyclized. The condensation reaction according to the first step is realized in a manner known per se [Houben-Weyl: Methoden der Organischen Chemie Vol. VIII/3, pages 137 to 147 (1952)]. The thus obtained 4-acetyl-4-carbamoyloxypiperidine derivative of formula (V) is preferably cyclized in the presence of a base. The cyclization may be carried out under the reaction conditions described for the step β) of process a). Alternatively, according to a preferred embodiment of this process, the 4-acetyl-4-carbamoyloxypiperidine derivative of the formula (V), obtained in the reaction of the 4-acetyl-4-hydroxypiperidine derivative of the formula (IV) with the isocyanate of formula R-NCO, is directly cyclized without isolation in the same reaction mixture, in the presence of a suitable base.

By using the process e) of the invention, the second step of the process d) is in principle followed.

If desired, the compounds of the formula (I) obtained by using the processes a) can be transformed to other compounds being within the scope of the formula (I) in a manner known per se.

Thus, on reacting a compound of the formula (I), wherein X means oxygen and $R^1$ together with $R^2$ represents a methylene group, with an amine of the formula R-NH$_2$, compounds of the formula (I) are obtained, wherein X means an >NR group and one of $R^1$ and $R^2$ is a hydroxyl group whereas the other one means a methyl group. This reaction may be carried out in a suitable solvent or without any solvent. Suitable solvents are e.g.: aliphatic, alicyclic or araliphatic alcohols such as ethanol, butanol, cyclohexanol, benzyl alcohol; aliphatic or aromatic hydrocarbons such as hexane, heptane, xylene, chlorobenzene or nitrobenzene; ethers, e.g. dioxane or di-n-butyl ether; and tertiary organic bases, e.g. picoline, triethylamine or pyridine; though an excess of an amine of the formula R-NH$_2$ may also serve as a solvent for the reaction. This procedure may be carried out at a temperature between room temperature and the boiling point of the reaction mixture, preferably under an inert gas, e.g. argon or nitrogen.

If desired, the compounds of the formula (I) containing a hydroxyl and a methyl group, respectively as $R^1$ and $R^2$, can be dehydrated to compounds of the formula (I), wherein $R^1$ and $R^2$ together represent a methylene group. The dehydration may be achieved under normal or reduced pressure by using commonly known procedures. Isocyanates, aliphatic carboxylic acids, aliphatic or aromatic carboxylic acid anhydrides, Lewis acids, sulfuric acid or aromatic sulfonic acids can be employed for the dehydration. This reaction is preferably performed in an organic solvent. Suitable solvents are e.g. aromatic hydrocarbons such as benzene, toluene or xylene; ethers such as dioxane, di-n-butyl ether; or aliphatic carboxylic acids such as acetic acid. According to a preferred embodiment of this reaction, e.g. a mixture of glacial acetic acid and acetic anhydride may be used or the dehydration may be carried out in xylene in the presence of p-toluenesulfonic acid while the water formed in the reaction is azeotropically distilled out.

If desired, a water molecule can be introduced in an addition reaction into the compounds of formula (I), wherein $R^1$ and $R^2$ together stand for a methylene group, to give compounds of the formula (I) containing a hydroxyl and a methyl group, respectively as $R^1$ and $R^2$. This hydration reaction is accomplished in an aqueous medium, in the presence of a mineral land/or organic acid as acid e.g. hydrogen halides, sulfuric, phosphoric, formic acid, aromatic sulfonic acids, oxalic or trifluoroacetic acid and the like may be employed. This reaction is carried out between 5° C. and the boiling point of the reaction mixture.

From the obtained compounds of formula (I), wherein $R^3$ represents a benzyl or benzyloxycarbonyl group, these groups can be removed e.g. by a reductive cleavage to obtain compounds of the formula (I), wherein $R^3$ means hydrogen. This reduction may preferably be carried out by catalytic hydrogenation. As hydrogenating catalysts e.g. metal such as ruthenium, palladium, platinum, nickel, iron, cobalt chromium, zinc, tungsten, molybdenum and the like as well as their oxides and sulfides may be employed. The catalytic hydrogenation may also be carried out by using a catalyst previously precipitated onto the surface of a carrier. Such carriers may be e.g. carbon, silicon dioxide, aluminum oxide as well as carbonates and sulfates of the alkaline-earth metals. This reduction is suitably accomplished in the presence of palladium-on-charcoal by hydrogenation in an inert solvent. Lower aliphatic alcohols, ethers, esters as well as aliphatic, cycloaliphatic or aromatic hydrocarbons or their mixtures may be used as solvents. The hydrogenation may be accomplished under atmospheric or higher pressure at a temperature between 20° C. and the boiling point of the reaction mixture. After termination of the reaction the catalyst is filtered off, the filtrate is evaporated and, if desired, the product obtained is purified e.g. by recrystallization. According to a preferred embodiment of the reduction, this process is performed by the means of catalytic transfer hydrogenation which is well known in the literature by using a hydrogen donor substance such as formic acid, hydrazine and the like in the presence of palladium-on-charcoal catalyst. A formyl group as $R^3$ can reductively be cleaved or it can be removed by using hydrazine or hydroxylamine in the presence of a weak acid such as acetic acid. This reaction may be carried out in inert organic solvents such as e.g.: lower alkanols, e.g. methanol or ethanol; or in acid amides; e.g. dimethylacetamide; or in ethers such as dioxane; or in the mixtures of the above solvents. The reaction medium may contain water, too. The temperature is preferably increased for accelerating the reaction. Thus, this reaction is preferably carried out at a temperature between 40° C. and the boiling point of the reaction mixture.

Hydrogen as $R^3$ in the compounds of formula (I) may be replaced by an other group by using methods known per se; it can be replaced e.g. by a benzyl group on reacting it with a benzyl halide, preferably benzyl chloride or bromide, suitably in the presence of a convenient base such as an alkali metal or alkaline earth metal carbonate or hydrogen carbonate, a tertiary organic base or an excess of the compound of formula (I) which are useful for binding the acid formed in the reaction. Little amount of an alkali metal iodide, e.g. potassium iodide may be used for promoting this reaction.

Hydrogen as $R^3$ may be replaced by a ($C_{1-4}$alkoxy)-carbonyl, phenoxycarbonyl or benzyloxycarbonyl group in the reaction with a reactive carboxylic acid derivative containing such a group. A suitable chloroformate ester may be used as a reactive carboxylic acid derivative. This reaction is conveniently carried out in the presence of a base being useful for binding the acid formed in the reaction. For this purpose e.g. the bases listed above may be employed. The reaction is accomplished by using methods commonly known from the literature.

Hydrogen as $R^3$ may be replaced by a formyl group by using a reactive formic acid derivative. Chloride, imidazolide or preferably a mixed anhydride of formic acid may e.g. be used as reactive derivatives. For the formylation of compounds of the formula (I) e.g. the mixed anhydride of formic acid with acetic acid may be used. However, this reaction may be carried out by using any other commonly known N-acylating process, too.

Hydrogen as $R^3$ may be replaced by a $C_{1-6}$alkylcarbamoyl, piperidin-1-ylcarbonyl, 4-methylpiperazin-1-ylcarbonyl or 2-chloro-3-nicotinoylcarbamoyl group through the reaction of a suitably substituted chloroformic acid amide or isocyanate. This reaction is carried out in an appropriate inert solvent, preferably in the presence of a base under an inert gas, e.g. argon or nitrogen. Aromatic hydrocarbons such as benzene, toluene or xylene; ethers such as diethyl ether, diisopropyl ether or dioxane; halogenated hydrocarbons such as methylene chloride, 1,2-dichloroethane or chloroform; nitriles, e.g. acetonitrile; acid amides such as N-methyl-2-pyrrolidone; tertiary organic bases, e.g. picolines, triethylamine or pyridine, may be used as solvents. The above mentioned inorganic and tertiary organic bases are useful acid binding agents. The reaction may be carried out at a temperature between 0° C. and the boiling point of the reaction mixture. The reaction with an acyl isocyanate, e.g. 2-chloro-3-nicotinoyl isocyanate may be realized in such a way, too, that the isocyanate compound is prepared in situ and the compound of the formula (I) to be acylated is added to the reaction mixture containing the isocyanate. Thus, 2-chloro-3-nicotinoyl isocyanate can be prepared e.g. by reacting 2-chloronicotinic acid amide with oxalyl chloride in an inert solvent such as 1,2-dichloroethane.

Compounds containing a phenoxycarbonyl group as $R^3$ can be prepared also from the compounds of formula (I) containing a benzyl groups as $R^3$ by reacting the latter ones with phenyl chloroformate. On reacting compounds of the formula (I) containing a phenoxycarbonyl group as $R^3$ with N-(2-hydroxyethyl)piperazine, compounds of the formula (I) containing a 4-(2-hydroxyethyl)piperazin-1-ylcarbonyl group as $R^3$ are obtained.

If desired, the compounds of the formula (I) may be converted to their acid addition salts or quaternary ammonium salts by using methods known per se. For the preparation of acid addition salts, inorganic or organic acids such as hydrogen halides, e.g. hydrochloric acid and hydrobromic acid as well as sulfuric, phosphoric, formic, acetic, propionic, oxalic, glycolic, maleic, fumaric, succinic, tartaric, ascorbic, citric, malic, salicyclic, lactic, benzoic, cinnamic, aspartic, glutamic, N-acetylaspartic or N-acetylglutamic acid, furthermore alkanesulfonic acids such as methanesulfonic acid or arenesulfonic acids, e.g. p-toluenesulfonic acid and the like, may be used.

The salt formation can be carried out e.g. in such a way that the corresponding acid is added to the solution of the compound of formula (I) in an inert solvent, e.g. ethanol, and the salt formed is precipitated by adding preferably a water-immiscible organic solvent, e.g. ethyl ether. For the preparation of quaternary ammonium salts a lower alkyl, alkenyl or benzyl halide or an alkyl sulfate may preferably be employed. The quaternization is suitably performed in an organic solvent such as acetone, acetonitrile, ethanol or their mixtures, at a temperature range from room temperature up to the boiling point of the solvent. The acid addition or quaternary ammonium salt obtained may be isolated e.g. by filtration and, when necessary, purified by recrystallization.

Conversely, the corresponding bases can be liberated from their salts by an alkaline treatment.

The starting substances are known or can be prepared analogously to methods known from the literature.

The compounds of the formulae (II) and (V) are obtained by reacting the 4-hydroxypiperidine derivatives of the formula (III) or (IV), respectively with isocyanates of the formula R-NCO by using a method known per se [see e.g.: Houben-Weyl: Methoden der Organischen Chemie Vol. VIII/3, pages 17 to 147 (1952)].

The compounds of the formula (III) can be prepared e.g. by the ethynylation reaction of the appropriately substituted 4-piperidine derivatives according to e.g. the Hungarian patent specification No. 166,769 or by using a method described in: Farmaco (Pavia) Ed. Sci. 12 34 (1957).

The 4-acetyl-4-hydroxypiperidine derivatives of the formula (V) can be obtained e.g. by the hydration of the corresponding 4-ethynyl-4-hydroxypiperidine derivatives of the formula (III) [see e.g.: Houben-Weyl: Methoden der Organischen Chemie Vol. VII/2a, pages 826 to 835 (1973)] or by the alkaline treatment of the corresponding 4-methylene-2-oxo-1,3-dioxa-8-azaspiro[4,5]-decane derivatives of the formula (I).

The novel compounds of formula (I) according to the invention are useful intermediates in the synthesis of therapeutically active spirodecane derivatives (which are described e.g. in the Hungarian patent application Nos. 4093/89, 4094/89 and 4095/89 and the corresponding concurrently filed U.S. applications Ser. Nos. 566,276, 566,273, 566,278 and 566,279 and Ser. No. 566,275.

The compounds of the Formula (I) where $R^1$ and $R^2$ together form a methylene group may be converted to compounds of the Formula (VII)

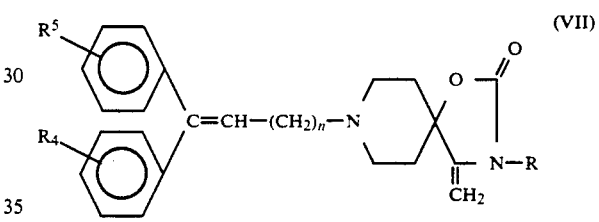

(VII)

$R^4$ and $R^5$, which are the same or different, represent hydrogen, one or more halogen(s), $C_{1-4}$alkyl, $C_{1-4}$alkoxy, trihalomethyl group or hydroxy group optionally esterified by a $C_{1-4}$alkanoic acid; and
n is 1 or 2,
by reaction, with a diphenylalkene derivative of the formula (VIII),

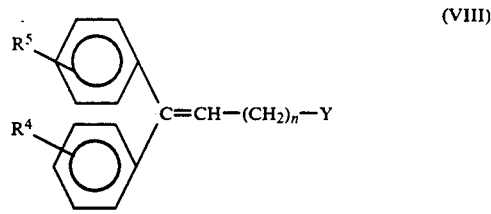

(VIII)

wherein Y means halogen, $C_{1-4}$-alkylsulfonyloxy or arylsulfonyloxy group.

The compounds of the Formula (VII) are useful to treat acute and chronic schizophrenia, manic depressive pyschosis, agitation, and pyschomotor disquiet. Preparation for compounds of the Formula (VII) is examplified in examples 37 to 48.

The invention also relates to a method for treating epileptic and allergic diseases and high (increased) lipid levels. This method comprises administering a therapeutically effective amount of an active ingredient of the formula (I) or a pharmaceutically acceptable acid addition or quaternary ammonium salt thereof to the patient.

The invention is illustrated in detail by the aid of the following non-limiting Examples.

EXAMPLE 1

Preparation of
8-benzyl-4-methylene-2-oxo-1,3-dioxa-8-azaspiro[4,5]-decane

Dry gaseous hydrogen chloride is introduced at 20° to 50° C. during 2.5 to 3 hours into a solution containing 31.4 g of 1-benzyl-4-butylcarbamoyloxy-4-ethynyl-piperidine in 157 ml of anhydrous dioxane. After standing overnight the reaction mixture is evaporated in a water bath of 40° to 50° C. temperature under reduced pressure. After adding 200 ml of water to the evaporation residue the base is liberated by sodium hydrogen carbonate. After filtration the solid precipitate is washed to chloride-free with water and dried. The crude product obtained is recrystallized from n-hexane under clarifying by activated carbon to give the title compound in 80.6% yield, m.p.: 65°–67° C.

Analysis: Calculated for $C_{15}H_{17}NO_3$ C 69.48; H 6.61; N 5.40%; found: C 69.65; H 6.51; N 5.63%.

EXAMPLE 2

Preparation of
8-benzyl-4-methylene-2-oxo-1,3-dioxa-8-azaspiro[4,5]-decane 5.16 g of 1-benzyl-4-carbamoyloxy-4-ethynylpiperidine are stirred in 30 ml of 30% by weight solution of hydrogen bromide in acetic acid at room temperature for 6 hours. After evaporating the solvent under reduced pressure and adding 50 ml of water to the residue the base is liberated by sodium hydrogen carbonate. The solid product obtained is filtered, washed to bromide-free with water, dried and recrystallized from n-hexane to give the title compound in 59.3% yield the physical characteristics of which are in agreement with those given in Example 1.

EXAMPLE 3

Preparation of
3-[2-(3,4-dimethoxyphenyl)ethyl]-8-benzyl-4-hydroxy-4-methyl-2-oxo-1-oxa-3,8-diazaspiro[4,5]decane 19.9 g of 2-(3,4-dimethoxyphenyl)ethylamine are portionwise added to a solution of 25.9 g of 8-benzyl-4-methylene-2-oxo-1,3-dioxa-8-azaspiro[4,5]decane in 35 ml of anhydrous xylene under stirring. Meanwhile the temperature of the reaction mixture increases to 35° to 40° C. The reaction mixture is left to stand at room temperature overnight, then the crystalline reaction mixture is diluted with n-heptane and filtered. The solid precipitate obtained is recrystallized from ethanol to obtain the title compound in 94% yield, m.p.: 181°–183° C.

Analysis: Calculated for $C_{25}H_{32}N_2O_5$ C 68.16; H 7.32; N 6.36%; found: C 68.35; H 7.18; N 6.50%.

By using the appropriate starting substances the following compounds can be prepared in an analogous manner as described in the above Example.

8-Benzyl-3-decyl-4-hydroxy-4-methyl-2-oxo-1-oxa-3,8-diazaspiro[4,5]decane, m.p.: 111°–120° C.;

8-Benzyl-3-heptyl-4-hydroxy-4-methyl-2-oxo-1-oxa-3,8-diazaspiro[4,5]decane, m.p.: 116°–117° C.;

8-Benzyl-3-butyl-4-hydroxy-4-methyl-2-oxo-1-oxa-3,8-diazaspiro[4,5]decane, m.p.: 122°–123° C. (the hydrochloride is precipitated by using an etheral hydrogen chloride solution, it melts about 260° C.); and 8-Benzyl-4-hydroxy-4-methyl-2-oxo-3-phenyl-1-oxa-3,8-diazaspiro[4,5]decane, m.p.: 203°–205° C. [hydrochloride m.p.: 284°–286° C. (with decomposition)].

EXAMPLE 4

Preparation of
8-benzyl-4-hydroxy-4-methyl-2-oxo-1-oxa-3,8-diazaspiro[4,5]decane A solution containing 13.2 g of 8-benzyl-4-methylene-2 2-oxo-1,3-dioxa-8azaspiro[4,5]decane in 130 ml of anhydrous ether is portionwise added to 130 ml of liquid ammonia under stirring and after stirring the reaction mixture for additional 30 minutes the ammonia is evaporated. The crystalline precipitate is filtered, washed with ether and dried to give the title product in 97.2% yield, m.p.: 162°–164° C.

Analysis: Calculated for $C_{15}H_{20}N_2O_3$ C 65.19; H 7.29; N 10.14%; found: C 65.24; H 7.43; N 10.28%.

The above reaction may be carried out also by using 25% aqueous ammonium hydroxide solution. The physical charcteristics of the product thus obtained are identical to those given above.

EXAMPLE 5

Preparation of
3,8-dibenzyl-4-methylene-2-oxo-1-oxa-3,8-diazaspiro[4,5]decane

A solution containing 34.8 g of 1-benzyl-4-benzylcarbamoyloxy-4-ethynylpiperidine and 1.1 g of sodium methoxide in 350 ml of anhydrous methanol is refluxed for 4 hours. After cooling down and maintaining the reaction mixture at 0° C. for 30 to 60 minutes the crystalline precipitate is filtered and recrystallized from methanol to obtain the title compound in 83% yield, m.p.: 113°–114° C.

Analysis: Calculated for $C_{22}H_{24}N_2O_2$ C 75.83; H 6.94; N 8.04%; found: C 75.71; H 7.03; N 8.20%.

EXAMPLE 6

Preparation of
8-benzyl-3-tert-butyl-4-hydroxy-4-methyl-2-oxo-1-oxa-3,8-diazaspiro[4,5]decane 8.3 g of 4-acetyl-1-benzyl-4-tert-butylcarbamoyloxypiperidine are refluxed in 100 ml of an ethanolic sodium ethoxide solution of 0.1 mole/liter concentration under stirring for 3 to 4 hours. After cooling down and adding 10% by weight aqueous ammonium chloride solution to the reaction mixture the most part of the solvent is distilled off under reduced pressure. After adding water to the residue the precipitate is filtered off, washed to chloride-free with water, dried and finally recrystallized from benzene to give the title compound in 78% yield, m.p.: 179°–181° C.

Analysis: Calculated for $C_{19}H_{28}N_2O_3$ C 68.64; H 8.49; N 8.43%; found: C 68.75; H 8.57; N 8.65%.

EXAMPLE 7

Preparation of
8-benzyl-3-n-heptyl-4-methylene-2-oxo-1-oxa-3,8-diazaspiro[4,5]decane The solution of 18.7 g of 8-benzyl-3-n-heptyl-4-hydroxy-4-methyl-2-oxo-1-oxa-3,8-diazaspiro[4,5]decane in 40 ml of benzyl alcohol is heated at 160° C. for 5 hours while the water formed in the reaction is azeotropically distilled off. Thereafter, the mixture is evaporated under reduced pressure. After taking up the residue in chloroform the solution is dried over anhydrous magnesium sulfate, filtered off and evaporated under reduced pressure. The crude product obtained is recrystallized from n-hexane under clarifying by activated carbon to obtain the title compound in 81% yield, m.p.: 47°–48° C.

Analysis: Calculated for $C_{22}H_{32}N_2O_2$ C 74.12; H 9.05; N 7.68%; found: C 74.33; H 9.14; N 7.68%.

EXAMPLE 8

Preparation of 3-benzyl-8-benzyloxycarbonyl-4-hydroxy-4-methyl-2-oxo-1-oxa-3,8-diazaspiro[4,5]decane 72 ml of aqueous hydrochloric solution of 3 mol/liter concentration are portionwise added during 20 to 30 minutes to the solution of 3.92 g of 3-benzyl-8-benzyloxycarbonyl-4-methylene-2-oxo-1-oxa-3,8-diazaspiro[4,5]-decane in 8 ml of 99% formic acid under stirring. The precipitate is filtered off, washed with water and dried. After recrystallization from ethanol the title compound is obtained in a yield of 89%; m.p.: 155°–157° C.

Analysis: Calculated for $C_{23}H_{26}N_2O_5$ C 67.30; H 6.38; N 6.82%; found: C 67.35; H 6.19; N 6.72%.

EXAMPLE 9

Preparation of 8-(2-chloronicotinoylcarbamoyl)-3-ethyl-4-hydroxy-4-methyl-2-oxo-1-oxa-3,8-diazaspiro[4,5]decane A solution of 11 g of 8-(2-chloronicotinoylcarbamoyl)-3-ethyl-4-methylene-2-oxo-1-oxa-3,8-diazaspiro[4,5]decane in 116 ml of hydrochloric acid of 1 mol/liter concentration is stirred at room temperature for 2 hours and then cooled down to 3° to 5° C. After adjusting the pH value of the reaction mixture to 6 to 7 by adding aqueous sodium hydrogen carbonate solution the precipitate is filtered and washed to chloride-free with water. The product obtained is recrystallized from a mixture of dimethylformamide and methylene chloride to give the title compound in 75% yield, m.p.: 195°–196° C.

Analysis: Calculated for $C_{17}H_{21}ClN_4O_5$ C 51.45; H 5.33; Cl 8.93; N 14.12%; found: C 51.60; H 5.51; Cl 8.84; N 14.25%.

EXAMPLE 10

Preparation of 8-benzyl-3-cyclohexyl-4-hydroxy-4-methyl-2-oxo-1-oxa-3,8-diazaspiro[4,5]decane hydrochloride and free base A solution of 10 g of 8-benzyl-3-cyclohexyl-4-methylene-2-oxo-1-oxa-3,8-diazaspiro[4,5]decane in 100 ml of aqueous hydrochloric acid of 0.03 mol/liter concentration is vigorously stirred at room temperature for 20 minutes. The precipitate is filtered, washed with ice-cold eater and then dried at room temperature over solid potassium hydroxide under reduced pressure to obtain the title hydrochloride in 97% yield, m.p.: 308°–310° C. (with decomposition).

After adding an equivalent amount of aqueous N sodium hydroxide solution to the hydrochloride, the base liberated is extracted into methylene chloride, the organic phase is dried over anhydrous sodium sulfate and evaporated under reduced pressure. The residue is recrystallized from a mixture of chloroform and benzene to give the title base in 95% yield, m.p.: 207°–208° C.

Analysis: Calculated for $C_{21}H_{30}N_2O_3$ C 70.36; H 8.43; N 7.81%; found: C 70.30; H 8.61; N 7.9%.

By using the appropriate starting substances the following compounds can be prepared in an analogous manner as described in Examples 8, 9 or 10.

8-(2-Chloronicotinoylcarbamoyl)-3,4-dimethyl-4-hydroxy-2-oxo-1-oxa-3,8-diazaspiro[4,5]decane, m.p.: 191°–193° C.;

3-tert-Butyl-4-hydroxy-4-methyl-2-oxo-8-phenoxycarbonyl-1-oxa-3,8-diazaspiro[4,5]decane, m.p.: 164°–165° C.;

8-Benzyl-3-(4-chlorophenyl)-4-hydroxy-4-methyl-2-oxo-1-oxa-3,8-diazaspiro[4,5]decane hydrochloride, m.p.: 298°–299° C.;

8-Benzyl-4-hydroxy-4-methyl-2-oxo-3-propyl-1-oxa-3,8-diazaspiro[4,5]decane hydrochloride, m.p.: 256°–257° C.;

3-Benzyl-8-tert-butylcarbamoyl-4-hydroxy-4-methyl-2-oxo-1-oxa-3,8-diazaspiro[4,5]decane, m.p.: 222°–224° C.;

8-Ethylcarbamoyl-4-hydroxy-4-methyl-2-oxo-3-phenyl-1-oxa-3,8-diazaspiro[4,5]decane, m.p.: 234°–236° C.;

3-Cyclohexyl-4-hydroxy-4-methyl-2-oxo-8-propylcarbamoyl-1-oxa-3,8-diazaspiro[4,5]decane, m.p.: 210°–212° C.;

3-Butyl-4-hydroxy-4-methyl-2-oxo-8-phenoxycarbonyl-1-oxa-3,8-diazaspiro[4,5]decane, m.p.: 136°–137° C.;

8-Benzyl-3-ethyl-4-hydroxy-4-methyl-2-oxo-1-oxa-3,8-diazaspiro[4,5]decane hydrochloride, m.p.: 268°–269° C.

EXAMPLE 11

Preparation of 8-benzyl-4-hydroxy-3,4-dimethyl-2-oxo-1-oxa-3,8-diazaspiro[4,5]decane trifluoroacetate and free base The solution containing 1.4 g of 8-benzyl-3-methyl-4-methylene-2-oxo-1-oxa-3,8-diazaspiro[4,5]decane in the mixture of 10 ml of water and 1.14 g of trifluoroacetic acid is stirred at room temperature for 15 minutes. The crystalline precipitate is filtered, washed with water and dried to give the title substance in 97% yield, m.p.: 147°–148° C.

The base is liberated by adding sodium hydroxide solution to its trifluoroacetate salt and melts at 161°–163° C.

Analysis of the base Calculated for $C_{16}H_{22}N_2O_3$ C 66.18; H 7.64; N 9.65%; found: C 66.32; H 7.58; N 9.78%.

EXAMPLE 12

Preparation of 8-benzyl-3-(4-chlorophenyl)-4-methylene-2-oxo-1-oxa-3,8-diazaspiro[4,5]decane and hydrogen fumarate A mixture containing 12.50 g of 1-benzyl-4-ethynyl-4-hydroxypiperidine, 9.21 g of 4-chlorophenyl isocyanate and 0.4 g of anhydrous sodium acetate is stirred under argon. The reaction is exothermic, therefore the reaction mixture is cooled in such a way that a highest temperature of 140° C. is maintained. After 2 hours the reaction mixture is cooled to room temperature, dissolved in 150 ml of chloroform, the chloroformic phase is washed with water, dried over anhydrous sodium sulfate and then evaporated under reduced pressure. The crude product obtained as evaporated residue is recrystallized from acetonitrile to obtain the pure title substance in 84% yield, m.p.: 189°–191° C.

Analysis: Calculated for $C_{21}H_{21}ClN_2O_2$ C 68.38; H 5.74; Cl 9.61; N 7.59%; found: C 68.53; H 5.81; Cl 9.55; N 7.63%.

An equimolar amount of fumaric acid dissolved in ethanol is added to a benzene solution of the base to obtain the hydrogen fumarate salt as a crystalline precipitate which is then filtered off and dried, m.p.: 230°–232° C.

EXAMPLE 13

Preparation of
8-benzyl-3-n-butyl-4-methylene-2-oxo-1-oxa-3,8-diazaspiro[4,5]decane and dihydrogen citrate 2.15 g of 1-benzyl-4-ethynyl-4-hydroxypiperidine are boiled under reflux with 12.9 g of n-butyl isocyanate in the presence of 0.4 g of anhydrous potassium acetate in 66 ml of 2-picoline under nitrogen for 6 hours. After evaporating 2-picoline under reduced pressure and dissolving the residue in benzene, the organic solution is washed with water and dried over anhydrous magnesium sulfate. After filtration on an aluminum oxide layer the benzene solution is evaporated under reduced pressure. The crude product obtained is recrystallized from n-heptane to give the pure title substance in 78.5% yield, m.p.: 57°–58° C.

Analysis: Calculated for $C_{19}H_{26}N_2O_2$ C 72.58; H 8.33; N 8.91%; found: C 72.55; H 8.53; N 9.06%.

An equimolar amount of anhydrous citric acid dissolved in ethanol is added to the base dissolved in anhydrous ether and the solution is diluted with ether to give the dihydrogen citrate salt as crystalline precipitate which is filtered off and dried, m.p.: 148°–150° C.

By using the appropriate starting substances the following compounds can be prepared in an analogous way as described in Examples 12 or 13.

8-Formyl-4-methylene-2-oxo-3-phenyl-1-oxa-3,8-diazaspiro[4,5]decane, m.p.: 171°–172° C.;

8-Benzyloxycarbonyl-4-methylene-2-oxo-3-phenyl-1-oxa-3,8-diazaspiro[4,5]decane, m.p.: 145°–146° C.;

4-Methylene-2-oxo-3-phenoxycarbonyl-3-phenyl-1-oxa-3,8-diazaspiro[4,5]decane, m.p. 208°–210° C.;

8-Benzyl-3-cyclohexyl-4-methylene-2-oxo-1-oxa-3,8-diazaspiro[4,5]decane, m.p.: 128°–130° C. (the hydrogen fumarate salt melts at 207°–208° C.);

8-Benzyl-3-ethyl-4-methylene-2-oxo-1-oxa-3,8-diazaspiro[4,5]decane, m.p.: 103°–104° C. (hydrogen maleate salt m.p.: 184°–186° C.);

8-Benzyl-3-tert-butyl-4-methylene-2-oxo-1-oxa-3,8-diazaspiro[4,5]decane, m.p.: 116–117 (dihydrogen citrate salt m.p.: 132°–133° C.);

8-Benzyl-4-methylene-2-oxo-3-phenyl-1-oxa-3,8-diazaspiro[4,5]decane, m.p.: 134°–135° C.;

8-Benzyl-3-isopropyl-4-methylene-2-oxo-1-oxa-3,8-diazaspiro[4,5]decane, m.p.: 96°–97° C.;

8-Benzyl-3-methyl-4-methylene-2-oxa-3,8-diazaspiro[4,5]decane hydrogen maleate, m.p.: 210°–211° C.;

8-Benzyl-4-methylene-2-oxo-3-propyl-1-oxa-3,8-diazaspiro[4,5]decane dihydrogen citrate, m.p.: 168°–171° C.

EXAMPLE 14

Preparation of
3,4-dimethyl-4-dihydroxy-2-oxo-8-phenoxycarbonyl-1-oxa-3,8-diazaspiro[4,4]decane A solution of 1.6 g of methyl isocyanate in 5 ml of pyridine is dropwise added to a solution containing 5.3 g of 4-acetyl-4-hydroxy-1-phenoxycarbonylpiperidine and 0.2 g of sodium methoxide in 10 ml of pyridine under argon while stirring. The reaction is exothermic. After the addition the reaction mixture is refluxed for 2 to 3 ours, then the solvent is evaporated under reduced pressure. After taking up the evaporation residue in benzene the solution is washed with water to neutral and evaporated under reduced pressure to give the crude title product which is then recrystallized from ethyl acetate under clarifying by activated carbon to give the crystalline title compound in 61% yield, m.p.: 166°–168° C.

Analysis: Calculated for $C_{16}H_{20}N_2O_5$ C 59.99; H 6.29; N 8.74%; found: C 60.17; H 6.18; N 8.86%.

EXAMPLE 15

Preparation of
3-tert-butyl-8-ethylcarbonyl-4-methylene-2-oxo-1-oxa-3,8-diazaspiro[4,5]decane A mixture containing 4.3 g of 4-acetyl-1-ethoxycarbonyl-4-hydroxypiperidine, 6.0 g of tert-butyl isocyanate and 1 ml of triethylamine is refluxed under nitrogen for 6 hours. After cooling down and adding 50 ml of chloroform to the reaction mixture the organic phase is washed with water to neutral, then the solvent is evaporated under reduced pressure. The crude product obtained as evaporation residue is recrystallized from isopropyl ether to give the title substance in 44% yield, m.p.: 104°–105° C.

Analysis: Calculated for $C_{15}H_{24}N_2O_4$ C 60.79; H 8.16; N 9.45%; found C 60.66; H 8.23; N 9.61%.

EXAMPLE 16

Preparation of
3-methyl-4-methylene-2-oxo-1-oxa-3,8-diazaspiro[4,5]-decane 2 g of catalyst containing 10% by weight of palladium on charcoal are suspended in 20 ml of water and added to the solution of 20.0 g of 8-benzyl-3-methyl-4-methylene-2-oxo-1-3,8-diazaspiro[4,5]decane in 180 ml of methanol at 0° to 5° C. under nitrogen while stirring. Thereafter, 4.9 ml of an aqueous hydrazine solution of 48 g/100 ml concentration are introduced to the mixture which is then gently boiled under reflux. The progress of the reaction is followed by thin layer chromatography (TLC). After termination of the reaction (10 to 15 minutes) the mixture is cooled down, the catalyst is filtered off and washed with methanol. The methanolic washings are combined with the methanolic solution and the solvent is evaporated under reduced pressure. After recrystallizing the evaporation residue from a mixture of ethyl acetate with isopropyl ether the title compound is obtained in 94% yield, m.p.: 92°–93° C.

Analysis: Calculated for $C_9H_{14}N_2O_2$ C 59.32; H 7.74; N 15.37%; found: C 59.55; H 7.76; N 15.49%.

EXAMPLE 17

Preparation of
4-methylene-2-oxo-3-n-propyl-1-oxa-3,8-diazaspiro[4,5]decane

A suspension containing 0.5 g of 10% by weight palladium-on-carcoal catalyst in 5 ml of water is added to the solution of 5.0 g of 8-benzyloxycarbonyl-4-methylene-2-oxo-3-n-propyl-1-oxa-3,8-diazaspiro[4,5]-decane in 45 ml of methanol at 0° C. under argon while stirring. To this mixture 1 ml of 45.8% aqueous hydrazine solution is introduced and the reaction mixture is refluxed for 10 to 15 minutes. After cooling down to room temperature and filtering off the catalyst the solvent is evaporated under reduced pressure and the crude evaporation residue is recrystallized from benzene to give the title compound in 95% yield, m.p.: 96°–97° C.

Analysis: Calculated for $C_{11}H_{18}N_2O_2$ C 62.83; H 8.63; N 13.32%; found: C 63.00; H 8.57; N 13.47%.

By using the appropriate starting substances the following compounds can be prepared in an analogous way as described in Example 17.

3-Ethyl-4-methylene-2-oxo-1-oxa-3,8-diazaspirao[4,5]-decane, m.p.: 106°–108° C.;
3-isopropyl-4-methylene-2-oxo-1-3,8-diazaspirao[4,5]-decane, m.p. 151°–152° C.;
4-methylene-3-(1-naphthyl)-2-oxo-1-3,8-diazaspiro[4,5-decane, m.p.: 208°–209° C.;
3-butyl-4-methylene-2-oxo-1-oxa-3,8-diazaspiro[4,5]-decane, oil;
4-methylene-2-oxo-3-phenyl-1-oxa-3,8-diazaspiro[4,5]decane, m.p.: 185°–186° C.;
3-tert-Butyl-4-methylene-2-oxo-1-oxa-3,8-diazaspiro[4,5]-decane, m.p.: 138°–139° C.;
3-heptyl-4-hydroxy-4-methyl-2-oxo-1-oxa-3,8-diazaspiro[4,5]-decane, m.p.: 139°–140° C.;
3-[2-(3,4-dimethoxyphenyl)ethyl]-4-hydroxy-4-methyl-2-oxo-1-oxa-3,8-diazaspiro[4,5]decane, m.p. 190°–191° C.;
3-benzyl-4-methylene-2-oxo-1-oxa-3,8-diazaspiro[4,5]-decane, m.p.: 77°–79° C.;
3-heptyl-4-methylene-2-oxo-1-oxa-3,8-diazaspiro[4,5]-decane, oil;
3-decyl-4-methylene-2-oxo-1-oxa-3,8-diazaspiro[4,5]-decane, oil;
3-cyclohexyl-4-methylene-2-oxo-1-oxa-3,8-diazaspiro[4,5]decane, m.p.: 141°–142° C.;
3-[2-(3,4-dimethoxyphenyl)ethyl]-4-methylene-2-oxo-1-oxa-3,8-diazaspiro[4,5]decane, m.p.: 107°–109° C.

EXAMPLE 18

Preparation of
4-methylene-2-oxo-3-phenyl-1-oxa-3,8-diazaspiro[4,5]-decane

A solution containing 5.4 g of 8-formyl-4-methylene-2-oxo-3-phenyl-1-oxa-3,8-diazaspiro[4,5]decane, 3.0 g of hydrazine monohydrate and 3.6 g of acetic acid in 54 ml of aqueous ethanol of 60% by volume concentration is stirred under argon at a temperature of 62°–65° C. The reaction is followed by TLC. After termination of the reaction the mixture is evaporated under reduced pressure. After taking up the residue in chloroform and saturated aqueous sodium hydrogen carbonate solution, the chloroformic phase is separated, washed to neutral, dried over anhydrous magnesium sulfate and evaporated under reduced pressure. The crude product obtained is recrystallized from ethyl acetate under clarifying by activated carbon to give the title compound in 41.0% yield, m.p.: 185°–186° C.

Analysis: Calculated for $C_{14}C_{16}N_2O_2$ C 68.83; H 6.60; N 11.47%; found: C 68.85; H 6.71; N 11.35%.

EXAMPLE 19

Preparation of
4-hydroxy-4-methyl-2-oxo-1-oxa-3,8-diazaspiro[4,5]-decane

A solution containing 4.2 g of 8-benzyl-1-hydroxy-4-methyl-2-oxo-1-oxa-3,8-diazaspiro[4,5]decane in 42 ml of 95% methanol is refluxed in the presence of 0.75 g of hydrazine hydrate and 0.42 g of 10% by weight palladium-on-charcoal catalyst under vigorous stirring for 30 minutes. After cooling the reaction mixture to room temperature the catalyst is filtered off, washed with methanol and after combining the filtrate with the washings, the solution is evaporated under reduced pressure. After thoroughly triturating the residue with acetone the crystalline product obtained is filtered off and dried to give the title compound in 9.5% yield, m.p.: 192°–194° C.

Analysis: Calculated for $C_8H_{14}N_2O_3$ C 51.60; H 7.58; N 15.04%; found: C 51.58; H 7.55; N 15.2%.

EXAMPLE 20

Preparation of
3,4-dimethyl-4-hydroxy-2-oxo-1-oxa-3,8-diazaspiro[4,5]decane hydrochloride A solution of 5.44 g of 8-benzyl-3-methyl-4-methylene-2-oxo-1-oxa-3,8-diazaspiro[4,5]decane in 40 ml of N hydrochloric acid is hydrogenated in the presence of 5.4 g of palladium-on-charcoal catalyst until the theoretical amount of hydrogen is consumed. After filtering off the catalyst the filtrate is evaporated to a volume of about 10 ml under reduced pressure and 40 ml of acetone are added. The crystalline precipitate is filtered off and dried to obtain the title compound in 87% yield, m.p.: 272 –274° C.

Analysis of the base: Calculated for $C_9H_{16}N_2O_3$ C 53.98; H 8.05; N 13.99%; found: C 54.16; H 8.15; N 14.20%.

EXAMPLE 21

Preparation of
3-decyl-4-hydroxy-4-methyl-2-oxo-1-oxa-3,8-diazaspiro[4,5]decane 4.0 g of 8-benzyl-3-decyl-4-methylene-2-oxo-1-oxa-3,8-diazaspiro[4,5]decane are stirred together with 4.0 g of 10% by weight palladium-on-carbon catalyst in 40 ml of 50% aqueous formic acid for 2 hours at room temperature. After filtering off the catalyst the solution is evaporated under reduced pressure, the residue is treated with aqueous sodium hydrogen carbonate solution and the solid product is filtered off. After recrystallizing this product from a mixture of chloroform with n-hexane the title substance is obtained in 78.0% yield, m.p. 139°–140° C.

Analysis: Calculated for $C_{18}H_{34}N_2O_3$ C 66.22; H 10.50; N 8.58%; found: C 66.31; H 10.64; N 8.41%.

EXAMPLE 22

Preparation of
8-benzyl-4-methylene-3-(1-naphthyl)-2-oxo-1-oxa-3,8-diazaspiro[4,5]decane A mixture of 11.8 g of 4-methylene-3-(1-naphthyl)-2-oxo-1-oxa-3,8-diazaspiro[4,5]decane, 5.8 ml of benzyl chloride, 4.2 g of anhydrous sodium hydrogen carbonate, 0.5 g of potassium iodide and 177 ml of methyl ethyl ketone is refluxed under argon while stirring for 18 hours. After termination of the reaction the mixture is cooled down and the solvent is evaporated under reduced pressure. After adding chloroform and water to the residue and separating the phases, the organic layer is washed with water to chloride-free, dried over anhydrous magnesium sulfate and evaporated under reduced pressure. After recrystallizing the residue under clarifying by activated carbon the title substance is obtained in 84% yield, m.p.: 130°–131° C.

Analysis: Calculated for $C_{25}H_{24}N_2O_2$ C 78.10; H 6.29; N 7.29%; found: C 78.19; H 6.37; N 7.37%.

EXAMPLE 23

Preparation of
8-benzyl-4-methylene-2-oxo-3-(4-toluenesulfonyl)-1-oxa-3,8-diazaspiro[4,5]-decane A mixture containing 3.2 g of 4-methylene-2-oxo-3-(4-toluenesulfonyl)-1-oxo-3,8-diazaspiro[4,5]decane, 2.1 g of benzyl bromide and 1.7 g of anhydrous potassium carbonate in 32 ml of methyl isobutyl ketone is refluxed under nitrogen while stirring for 8 hours. After cooling down the reaction mixture to room temperature the inorganic salts are filtered off and the filtrate is evaporated under reduced pressure. The residue is dissolved in 50 ml of benzene, washed to bromide-free and neutral with water, dried over anhydrous sodium sulfate fate and evaporated under reduced pressure. After recrystallizing the crude product obtained from ethanol the title substance is obtained in 84% yield, m.p.: 157°–158° C.

Analysis: Calculated for $C_{22}H_{24}N_{22}SO_4$ C 64.05; H 5.86; N 6.79; S 7.77%; found: C 64.15; H 5.84; N 6.88; S 7.64%.

EXAMPLE 24

Preparation of
8-benzoyloxycarbonyl-3-cyclohexyl-4-methylene-2-oxo-1-oxa-3,8-diazaspiro[4,5]decane 3.5 ml of benzyl chloroformate dissolved in 5 ml of chloroform are portionwise added to the solution containing 5.0 g of 3-cyclohexyl-4-methylene-2-oxo-1-oxa-3,8-diazaspiro[4,5]decane and 3.4 ml of triethylamine in 50 ml of chloroform with cooling under nitrogen, then the reaction mixture is stirred at room temperature for an additional 30 minutes. After adding water to the reaction mixture and separating the phases the chloroformic layer is washed to neutral with water, dried over anhydrous sodium sulfate, then the solvent is evaporated under reduced pressure. After recrystallization of the residue from ethanol the title compound is obtained in 83% yield, m.p.: 104°–105° C.

Analysis: Calculated for $C_{22}H_{28}N_2O_4$ C 68.72; H 7.34; N 7.29%; found: C 68.66; H 7.44; N 7.33%.

By using the appropriate starting substances the following compounds can be prepared in an analogous way as described in Example 24.

3-Ethyl-4-methylene-2-oxo-8-phenoxycarbonyl-1-oxa-3,8-diazaspiro[4,5]decane, m.p.: 98°–99° C.;
3-cyclohexyl-4-methylene-2-oxo-8-phenoxycarbonyl-1-oxa-3,8-diazaspiro[4,5]decane, m.p. 188°–189° C.; and
3-butyl-4-methylene-2-oxo-8-phenoxycarbonyl-1-oxa-3,8-diazaspiro[4,5]decane, m.p.: 94°–95° C.

EXAMPLE 25

Preparation of
8-formyl-4-methylene-3-n-propyl-2-oxo-1-oxa-3,8-diazaspiro[4,5]decane A solution containing 4.6 g of 4-methylene-2-oxo-3-n-propyl-1-oxa-3,8-diazaspiro[4,5]decane in 35 ml of chloroform is dropwise added to a formic acid-acetic acid mixed anhydride prepared from 4.4 ml of acetic anhydride and 2.2 ml of formic acid in situ, then the reaction mixture is stirred at room temperature for an additional 30 minutes. After neutralizing the reaction mixture by adding 8.4% by weight aqueous sodium hydrogen carbonate solution under stirring and separating the phases, the organic layer is washed with water, dried over anhydrous potassium carbonate and evaporated under reduced pressure. The residue is mixed with ether and filtered off to give the title substance in 96% yield, m.p.: 150°–151° C.

Analysis: Calculated for $C_{12}H_{18}N_2O_3$ C 60.48; H 7.61; N 11.76%; found C 60.54; H 7.73; N 11.80%.

By using the appropriate starting substances the following compounds can be prepared in an analogous manner as described in Example 25.

3-tert-Butyl-8-formyl-4-methylene-2-oxo-1-oxa-3,8-diazaspiro[4,5]decane, m.p.: 141°–142° C.; and
3-cyclohexyl-8-formyl-4-methylene-2-oxo-1-oxa-3,8-dioazaspiro[4,5]decane, m.p.: 212°–213° C.

EXAMPLE 26

Preparation of
8-butylcarbamoyl-3-methyl-4-methylene-2-oxo-1-oxa-3,8-diazaspiro[4,5]decane 2.25 ml of n-butyl isocyanate are dropped to a suspension of 3.64 g of 3-methyl-4-methylene-2-oxo-1-oxa-3,8-diazaspiro[4,5]decane in 18 ml of acetonitrile while stirring under argon. Since the reaction is exothermic, the temperature is maintained at 25° to 30° C. by cooling. After 15 minutes the reaction mixture is evaporated under reduced pressure. The white solid evaporation residue is recrystallized from ethyl acetate to obtain the title compound in 91.3% yield, m.p.: 129°–130° C.

Analysis: Calculated for $C_{14}H_{23}N_3O_3$ C 59.76; H 8.24; N 14.94%; found: C 59.63; H 8.28; N 15.04%.

By using the appropriate starting substances the following compounds can be prepared in an analogous manner as described in Example 26.

3-Cyclohexyl-4-methylene-2-oxo-8-propylcarbamoyl-1-oxa-3,8-diazaspiro[4,5]decane, m.p.: 157–158;
8-ethylcarbamoyl-4-methylene-2-oxo-3-phenyl-1-oxa-3,8-diazaspiro[4,5]decane, m.p.: 196°–197° C.;
3-benzyl-8-tert-butylcarbamoyl-4-methylene-2-oxo-1-oxa-3,8-diazaspiro[4,5]decane, m.p.: 158°–159° C.; and
8-butylcarbamoyl-3,4-dimethyl-4-hydroxy-2-oxo-1-oxa-3,8-diazaspiro[4,5]decane, m.p.: 152°–153° C.

EXAMPLE 27

Preparation of
4-methylene-8-(4-methylpiperazine-1-ylcarbonyl)-2-oxo-3-phenyl-1-oxa-3,8-diazaspiro[4,5]decane The solution of 3.9 g of 4-methylpiperazin-1-yl-carbonyl chloride in 5 ml of chloroform is dropwise added at a temperature between 0° and 5° C. to a solution containing 4.9 g of 4-methylene-2-oxo-3-phenyl-1-oxa-3,8-diazaspiro[4,5]decane and 7.4 ml of triethylamine in 74 ml of chloroform under stirring. Thereafter, the reaction mixture is stirred at room temperature for an additional 30 minutes. After termination of the reaction the chloroform phase is washed to chloride-free with water, dried over anhydrous sodium sulfate, then the solvent is evaporated under reduced pressure. After recrystallization of the crude product obtained from ethanol under clarifying by activated carbon the title compound is obtained in 83% yield, m.p.: 198°–199° C.

Analysis: Calculated for $C_{20}H_{26}N_4O_3$ C 64.84; H 7.07; N 15.12%; found: C 64.88; H 7.23; N 15.01%.

By using the appropriate starting substances the following compounds can be prepared in an analogous way as described in Example 27.

3-Methyl-4-methylene-8-(4-methylpiperazin-1-ylcarbonyl)-2-oxo-1-oxa-3,8-diazaspiro[4,5]decane, m.p.: 139°–140° C.;

3-cyclohexyl-4-methylene-8-(4-methylpiperazin-1-ylcarbonyl)-2-oxo-1-oxa-3,8-diazaspiro[4,5 decane, m.p.: 191°–192° C.;

4-methylene-2-oxo-3-(piperidin-1-ylcarbonyl)-3-propyl-1-oxa-3,8-diazaspiro[4,5]decane, m.p.: 105°–106° C.;

3-tert-butyl-4-methylene -2-oxo-8-(piperidin-1-ylcarbonyl)-1-oxa-3,8-diazaspiro[4,5]decane, m.p.: 149°–150° C.;

3-(4-chlorophenyl)-4-methylene-8-(morpholin-4-ylcarbonyl)-2-oxo-1-oxa-3,8-diazaspiro[4,5]decane, m.p.: 214°–215° C.;

4-methylene-8-(4-methylpiperazin-ylcarbonyl)-2-oxo-3-propyl-1-oxa-3,8-diazaspiro[4,5]decane, m.p.: 146°–147° C.; and 3-butyl-4-methylene-8-(4-methylpiperazin-1-ylcarbonyl)-2-oxo-1-oxa-3,8-diazaspiro[4,5]decane, m.p.: 113°–114° C.

EXAMPLE 28

Preparation of
8-(2-chloronicotinoylcarbamoyl)-3-isopropyl-4-methylene-2-oxo-1-oxa-3,8-diazaspiro[4,5]decane 5.8 g of oxalyl chloride are portionwise added to the solution of 6.2 g of 2-chloronicotinic acid amide in 150 ml of anhydrous 1,2-dichloroethane under stirring, then the reaction mixture is heated at 85° C. for 90 minutes. After cooling the mixture to 0° to 5° C. first 12.6 ml of triethylamine and then a solution of 8.4 g of 3-isopropyl-4-methylene-2-oxo-1-oxa-3,8-diazaspiro[4,5]decane in 42 ml of anhydrous 1,2-dichloroethane are portionwise added while maintaining the temperature between 20° and 30° C. The reaction mixture is stirred at room temperature for an additional 30 minutes, then extracted with 200 ml of N sodium hydroxide solution and then with 100 ml of water. After combining the aqueous extract is acidified to a pH value of 5.5 to 6 by adding acetic acid and the mixture is extracted with 1,2-dichloroethane. The organic solution is washed with water, dried over anhydrous magnesium sulfate and evaporated under reduced pressure. The residue is recrystallized from ethanol to give the title compound in 54% yield, m.p.: 186°–188° C.

Analysis: Calculated for $C_{18}H_{21}ClN_4O_4$ C 55.03; H 5.39; Cl 9.02; N 14.26%; found: C 55.15; H 5.57; Cl 9.14; N 14.12%.

By using the appropriate starting substances the following compounds can be prepared in an analogous manner as described in Example 28.

8-(2-Chloronicotinoylcarbamoyl)-3-methyl-4-methylene-2-oxo-1-oxa-3,8-diazaspiro[4,5]decane, m.p.: 196°–198° C.;

8-(2-chloronicotinoylcarbamoyl)-3-ethyl-4-methylene-2-oxo-1-oxa-3,8-diazaspiro[4,5]decane, m.p.: 202°–204° C.;

8-(2-chloronicotinoylcarbamoyl)-4-methylene-3-propyl-2-oxo-1-oxa-3,8-diazaspiro[4,5]decane, m.p.: 183°–184° C.;

3-tert-butyl-8-(2-chloronicotinoylcarbamoyl)-4-methylene-2-oxo-1-oxa-3,8-diazaspiro[4,5]decane, m.p.: 179°–181° C.;

3-n-butyl-8-(2-chloronicotinoylcarbamoyl)-4-methylene-2-oxo-1-oxa-3,8-diazaspiro[4,5]decane, m.p.: 166°–168° C.;

8-(2-chloronicotinoylcarbamoyl)-3-cyclohexyl-4-methylene-2-oxo-1-oxa-3,8-diazaspiro[4,5]decane, m.p.: 217°–218° C.; and 8-(2-chloronicotinoylcarbamoyl)-4-methylene-2-oxo-3-phenyl-1-oxa- 3,8-diazaspiro[4,5]decane, m.p.: 190°–192° C.

EXAMPLE 29

Preparation of
3-(4-chlorophenyl)-8-[4-(2-hydroxyethyl)piperazin-1-ylcarbonyl]-4-methylene-2-oxo-1-oxa-3,8-diazaspiro[4,5]decane A mixture containing 4.0 g of 3-(4-chlorophenyl)-4-methylene-2-oxo-8-phenoxycarbonyl-1-oxa-3,8-diazaspiro[4,5]decane and 6.13 ml of N-(2-hydroxyethyl)piperazine in 20 ml of ortho-xylene is refluxed under nitrogen for 60 hours. After cooling down, the reaction mixture is diluted with 20 ml of xylene and the organic solution is washed first with an aqueous saturated sodium chloride solution containing 5% by weight of sodium hydroxide and then with aqueous saturated sodium chloride solution. After drying over anhydrous magnesium sulfate and then evaporating the solvent under reduced pressure the crude product obtained is recrystallized from a mixture of benzene and hexane under clarifying by activated carbon to give the title compound in 67% yield, m.p.: 185°–186° C.

Analysis: Calculated for $C_{21}H_{27}ClN_4O_4$ C 57.99; H 6.27; Cl 8.15; N 12.88%; found: C 57.78; H 6.35; Cl 8.30; N 13.05%.

By using the appropriate starting substances the following compounds can be prepared in an analogous way as described in Example 29.

3-Butyl-8-[4-(2-hydroxyethyl)piperazin-1-ylcarbonyl]-4-methylene-2-oxo-1-oxa-3,8-diazaspiro[4,5decane, m.p.: 101.5°–102.5° C.;

8-[4-(2-hydroxyethyl)piperazin-1-ylcarbonyl]-3-methyl-4-methylene-2-oxo-1-oxa-3,8-diazaspiro[4,5]decane, m.p.: 177°–178° C.;

3-tert-butyl-8-[4-(2-hydroxyethyl)piperazin-1-ylcarbonyl]-4-methylene-2-oxo-1-oxa-3,8-diazaspiro[4,5]-decane, m.p.: 159°–160° C.;

3-cyclohexyl-4-methylene-2-oxo-8-piperidin-1-ylcarbonyl)-1-oxa-3,8-diazaspiro[4,5]decane, m.p.: 170–171° C.;

3-ethyl-4-methylene-8-(morpholin-4-ylcarbonyl)-2-oxo-1-oxa-3,8-diazaspiro[4,5]decane, m.p.: 160°–162° C.;

4-methylene-8-(morpholin-4-ylcarbonyl)-2-oxo-3-phenyl-1-oxa-3,8-diazaspiro[4,5]decane, m.p.: 215°–216° C.;

3-tert-butyl-4-methylene-8-(morpholin-4-ylcarbonyl)-2oxo-1-oxa-3,8-diazaspiro[4,5]decane, m.p.: 174°–175° C.;

3-cyclohexyl-4-methylene-8-(morpholin-4-ylcarbonyl)-2oxo-1oxa-3,8-diazaspiro[4,5]decane, m.p.: 202°–203° C.;

4-methylene-8-(morpholin-4-ylcarbonyl)-2-oxo-3-propyl-1-oxa-3,8-diazaspiro[4,5]decane, m.p.: 146°–147° C.;

3-butyl-4-methylene-8-(morpholin-4-ylcarbonyl)-2oxo-1-oxa-3,8-diazaspiro[4,5]decane, m.p.: 113°–114° C.;

3-ethyl-4-methylene-8-(4-methylpiperazin-1-ylcarbonyl)-2-oxo-1-oxa-3,8-diazaspiro[4,5]decane, m.p.: 140°–141° C.; and 3-tert-butyl-4-methylene-8-(4-methylpiperazin-1-ylcarbonyl)-2-oxo-1-oxa-3,8-diazaspiro[4,5]decane, m.p.: 143°–144° C.

EXAMPLE 30

Preparation of
3-tert-butyl-4-methylene-2-oxo-8-phenoxycarbonyl-1-oxa-3,8-diazaspiro[4,5]decane A solution of 3.6 g of phenyl chloroformate in 5 ml of methylene chloride are dropped to the solution of 6.3 g of 8-benzyl-3-tert-butyl-4-methylene-2-oxo-1-oxa-3,8-diazaspiro[4,5]decane in 30 ml of methylene chloride under argon at 0° C. while stirring, then the reaction mixture is stirred at room temperature for one additional hour. After termination of the reaction the mixture is diluted with 35 ml of methylene chloride, extracted with 4N sodium hydroxide solution and washed to neutral with water. After drying over anhydrous magnesium sulfate the solvent is evaporated under reduced pressure. After adding n-hexane to the residue the solid precipitate is filtered off and recrystallized from isopropanol to obtain the title substance in 82% yield, m.p.: 125°–126° C.

Analysis: Calculated for $C_{19}H_{24}N_2O_4$ C 66.26; H 7.02; N 8.13%; found: C 66.33; H 7.10; N 8.10%.

By using the appropriate starting substances the following compounds can be prepared in an analogous manner as described in Example 30.

3-Benzyl-8-benzyloxycarbonyl-4-methylene-2-oxo-1-oxa-3,8-diazaspiro[4,5]decane, oil;

8-benzyloxycarbonyl-3-butyl-4-methylene-2-oxo-1-oxa-3,8-diazaspiro[4,5]decane, m.p.: 47°–48° C.;

8-ethoxycarbonyl-3-methyl-4-methylene-2-oxo-1-oxa-3,8-diazaspiro[4,5]decane, m.p.: 121°–122° C.;

3-(3,4-dichlorophenyl)-4-methylene-2-oxo-8-phenoxycarbonyl-1-oxa-3,8-diazaspiro[4,5]decane, m.p.: 220°–222° C.;

3-methyl-4-methylene-2-oxo-8-phenoxycarbonyl-1-oxa-3,8-diazaspiro[4,5]decane, m.p.: 118°–119° C.; and 4-methylene-2-oxo-8-phenoxycarbonyl-3-propyl-1-oxa-3,8-diazaspiro[4,5]decane, m.p.: 96°–98° C.

EXAMPLE 31

Preparation of
8-benzyl-3,4-dimethyl-4-hydroxy-2-oxo-1-oxa-3,8-diazaspiro[4,5]decane and hydrochloride A suspension containing 5.2 g of 8-benzyl-4-methylene-2-oxo-1,3-dioxa-8-azaspiro[4,5]decane, 2.1 g of methylamine hydrochloride and 2.1 g of anhydrous powdered potassium carbonate in 11 ml of ethanol is stirred under nitrogen for 2 hours, then left to stand overnight. After adding water to the reaction mixture the crystalline precipitate is filtered off and washed with water. The crude product obtained is recrystallized from a mixture of acetone and diisopropyl ether to give the title compound in 88% yield with the same physical characteristics as given for the base in Example 10.

The hydrochloride is obtained by treating the base with an ethereal hydrogen chloride solution, m.p.: 277°–279° C.

By using the appropriate starting substance the following compound can be prepared in an analogous way as described in Example 31.

8-Benzyl-3-[2-(3,4-dihydroxyphenyl)ethyl]-4-hydroxy-4-methyl-2-oxo-1-oxa-3,8-diazaspiro[4,5]decane, m.p.: 105°–106° C.; the hydrogen maleate salt melts at 77° C.

EXAMPLE 32

Preparation of
8-benzyl-3-decyl-4-methylene-2-oxo-1-oxa-3,8diazaspiro[4,5]decane A mixture containing 6.2 g of 8-benzyl-3-decyl-3-hydroxy-4-methyl-2-oxo-1-oxa-3,8-diazaspiro[4,5]decane and 0.6 g of p-toluenesulfonic acid monohydrate in 63 ml of xylene is boiled by using a Dean-Stark device while azeotropically distilling out the water formed in the reaction. After termination of the reaction the mixture is cooled down, then the organic solution is extracted with an 5% by weight aqueous sodium hydroxide solution and with water up to neutral. The xylene phase is dried over anhydrous sodium sulfate and evaporated under reduced pressure. After recrystallization the evaporation residue from n-hexane under clarifying by activated carbon the title compound is obtained in 91% yield, m.p.: 51°–52° C.

Analysis: Calculated for $C_{25}H_{38}N_2O_2$ C 75.33; H 9.61; N 7.03%; found: C 75.41; H 9.69; N 7.15%.

By using the appropriate starting substances the following compounds can be prepared in an analogous way as described in Example 32.

8-Benzyl-3-[2-(3,4-dimethoxyphenyl)ethyl]-4-methylene-2-oxo-1-oxa-3,8-diazaspiro[4,5]decane, m.p.: 91°–92° C.; and 3,8-dibenzyl-4-methylene-2-oxo-1-oxa-3,8-diazaspiro[4,5]decane with the same physical characteristics as described in Example 4.

EXAMPLE 33

Preparation of
8-benzyl-4-methylene-2-oxo-1-oxa-3,8-diazaspiro[4,5]-decane

A solution containing 14.0 g of 8-benzyl-4-hydroxy-4-methyl-2-oxo-1-oxa-3,8-diazaspiro[4,5]decane in 210 ml of dioxane is boiled under nitrogen while azeotropically distilling out the water formed in the reaction. After termination of the reaction dioxane is evaporated under reduced pressure. The residue is recrystallized from ethanol under clarifying by activated carbon to give the title compound in 62% yield, m.p.: 169°–170° C.

Analysis: Calculated for $C_{15}H_{18}N_2O_2$ C 69.74; H 7.02; N 10.84%; found: C 69.92; H 7.18; N 10.78%.

EXAMPLE 34

Preparation of 8-benzyl-3-methyl-4-methylene-2-oxo-1-oxa-3,8-diazaspiro[4,5]decane A solution of 1.6 g of methylamine in 35 ml of xylene prepared at 0° C. is flown to the solution of 13.0 g of 8-benzyl-4-methylene-2-oxo-1,3-dioxa-8-azaspiro[4,5]decane in 30 ml of xylene under stirring. The reaction is exothermic, thus the temperature of the reaction mixture increases up to 55° to 60° C. Thereafter, the heterogeneous reaction mixture is heated to a temperature of 100° to 102° C., maintained at the same temperature for 10 minutes, then 0.2 g of p-toluenesulfonic acid monohydrate is added to the solution and the reaction mixture is boiled while the water formed in the reaction is azeotropically distilled out. After termination of the reaction the mixture is cooled down to room temperature, washed with 5% by weight aqueous sodium hydroxide solution and after separation the xylene phase is washed to neutral with water. The organic phase is dried over anhydrous sodium sulfate and evaporated under reduced pressure. The residue is recrystallized from a mixture of ethanol and diisopropyl ether under clarifying by activated carbon to obtain the title compound in 96.7% yield, m.p.: 96°–97° C.

Analysis: Calculated for $C_{16}H_{20}N_2O_2$ C 70.56; H 7.40; N 10.29%; found: C 70.58; H 7.55; N 10.14%.

EXAMPLE 35

Preparation of 8-benzyl-4-methylene-2-oxo-3-propyl-1-oxa-3,8-diazaspiro[4,5]decane After refluxing a solution containing 9.6 g of 8-benzyl-4-hydroxy-4-methyl-2-oxo-3-propyl-1-oxa-3,8-diazaspiro[4,5]decane in a mixture of 96 ml of acetic acid and 5.7 ml of acetic anhydride under argon for 5 hours the solvent is evaporated under reduced pressure. After adding 5% by weight aqueous sodium hydroxide solution to the residue up to a pH value of 10, the mixture is extracted with benzene and the organic phase is washed to neutral with water. After drying the organic phase over anhydrous sodium sulfate benzene is evaporated under reduced pressure. After recrystallizing the residue from diisopropyl ether the title compound is obtained in 86.4% yield, m.p.: 70°–71° C.

Analysis: Calculated for $C_{18}H_{24}N_2O_2$ C 71.97; H 8.05; N 9.33%; found: C 72.18; H 8.16; N 9.12%.

EXAMPLE 36

Pharmaceutical compositions containing e.g. the following components (ingredients) can be prepared from the novel compounds according to the invention.

a) Preparation of tablets 50.0 g of active ingredient are mixed together with 92 g of lactose, 40 g of potato starch, 4 g of polyvinylpyrrolidone, 6 g of talc, 1 g of magnesium stearate, 1 g of colloidal silicon dioxide (Aerosil) and 6 g of ultraamylopectin and, after wet granulation, the product obtained is compressed to tablets containing 50 mg of the active ingredient each.

b) Preparation of dragées

The tablets prepared as described above are covered in a manner known per se with a coat consisting of sugar and talc. The dragées are polished by using a mixture of bee wax and carnaube wax.

Each dragée weighes 250 mg.

c) Preparation of capsules 100 mg of active ingredient, 30 g of sodium lauryl sulfate, 280 g of starch, 280 g of lactose, 4 g of colloidal silicon dioxide (Aerosil) and 6 g of magnesium stearate are thoroughly mixed together and after sieving, the mixture obtained is filled into hard gelatin capsules containing 20 mg of the active ingredient each.

d) Preparation of suppositories 100.0 mg of active ingredient and 200.0 mg of lactose calculated for one suppository are thoroughly mixed together. 1700.0 mg of suppository base (e.g. Witepsol 4) are molten, cooled to 35° C. and the mixture of the active ingredient and lactose is mixed thereto by using a homogenizer. The product obtained is poured into cooled conic moulds. Each suppository weighes 2000 mg.

e) Preparation of a suspension

Components in 100 ml of the suspension:

| | |
|---|---|
| Active ingredient | 1.00 g |
| Sodium hydroxide | 0.26 g |
| Citric acid | 0.30 g |
| Nipagin (methyl 4-hydroxybenzoate sodium salt) | 0.10 g |
| Carbopol 940 (polyacrylic acid) | 0.30 g |
| 96% Ethanol | 1.00 g |
| Raspberry flavor | 0.60 g |
| Sorbitol (aqueous solution of 70%) | 71.00 g |
| Distilled water for injection purpose | up to 100.00 ml |

After adding Carbopol in little portions to the solution of nipagin and citric acid in 20 ml of distilled water under vigorous stirring, the solution obtained is left to stand for 10 to 12 hours. Subsequently, the amount given above of sodium hydroxide dissolved in 1 ml of distilled water, the aqueous solution of sorbitol and finally the ethanolic solution of the raspberry flavour are dropped in under stirring. The active ingredient is added in small portions to this mixture and suspended by using a submerged homogenizer. Finally, the suspension is supplemented to 100 ml by adding distilled water and the syrupy suspension is led through a colloid mill.

EXAMPLE 37

Preparation of 8-[4,4-bis(4-fluorophenyl)-3-butenyl]-4-methylene-2-oxo-3-phenyl-1-oxa-3,8-diazaspiro[4,5]decane A mixture containing 8.4 g of 4-methylene-2-oxo-3-phenyl-1-oxa-3,8-diazaspiro[4,5]decane, 18.4 g of 4,4-bis(4-fluorophenyl)-3-butenyl chloride, 0.3 g of potassium iodide, 9.2 g of anhydrous potassium carbonate and 81 ml of methyl isobutyl ketone is mildly refluxed under argon while stirring for 12 hours. After cooling down and filtering off the inorganic salts, the precipitate is washed with methyl isobutyl ketone, the filtrate is washed with water to neutral, dried over anhydrous magnesium sulfate, then the solvent is evaporated under reduced pressure. After triturating the evaporation residue with n-hexane, the precipitate is filtered and recrystallized from ethanol to give the title compound in 83.5% yield, m.p.: 136.5°-137.5° C.

Analysis Calculated for $C_{30}H_{28}F_2N_2O_2$ C 74.05; H 5.80; F 7.81; N 5.76%; found: C 74.19; H 5.85; F 7.74; N 5.83%.

EXAMPLE 38

Preparation of
8-[4,4-bis(4-fluorophenyl)-3-butenyl]-3-ethyl-4-methylene-2-oxo-1-oxa-3,8-diazaspiro[4,5]decane A mixture containing 7.8 g of 3-ethyl-4-methylene-2-oxo-1-oxa-3,8-diazaspiro[4,5]decane, 8.5 ml of anhydrous triethylamine, 80 ml of anhydrous methyl ethyl ketone, 3.0 g of potassium iodide and 16.7 g of 4,4-bis(4-fluorophenyl)-3-butenyl chloride is refluxed under nitrogen while stirring for 15 hours, then the solvent is distilled off under reduced pressure. After adding benzene and water to the residue, the benzene layer is washed with water to neutral, dried over anhydrous magnesium sulfate, filtered through an aluminum oxide bed and evaporated under reduced pressure. After recrystallizing the residue from ethanol, the title product is obtained in 68.7% yield, m.p.: 138°-139° C.

Analysis Calculated for $C_{26}H_{28}F_2N_2O_2$ C 7.21; H 6.44; F 8.66; N 6.39%; found: C 71.32; H 6.46; F 8.75; N 6.58%.

EXAMPLE 39

Preparation of
8-[4,4-bis(4-chlorophenyl)-3-butenyl]-3-butyl-4-methylene-2-oxo-1-oxa-3,8-diazaspiro[4,5]decane 10.7 g of 4,4-bis(4-chlorophenyl)-3-butenyl bromide are added to the solution of 4.5 g of 3-butyl-4-methylene-2-oxo-1-oxa-3,8-diazaspiro[4,5]decane in 45 ml of acetone containing 4.20 g of anhydrous potassium carbonate and 0.5 g of potassium iodide. The heterogeneous reaction mixture is refluxed under nitrogen while stirring for 5 hours. After evaporating the solvent under reduced pressure, water is added to the residue and extracted with benzene. The benzene phase is washed with water to halide-free, filtered through a silica gel bed and evaporated under reduced pressure. The residue is recrystallized from ethanol to give the title product in 79.0% yield, m.p.: 110°-111° C.

Analysis Calculated for $C_{28}H_{32}Cl_2N_2O_2$ C 67.33; H 6.46; Cl 14.20; N 5.61%; found: C 67.50; H 6.44; Cl 14.25; N 5.80%.

By using appropriate starting substances the following compounds are prepared analogously to the preceding Example:

8-[4,4-bis(4-fluorophenyl)-3-butenyl]-3-methyl-4-methylene-2-oxo-1-oxa-3,8-diazaspiro[4,5]decane, m.p.: 127.5°-128.5° C.;

8-[3-(4-acetyloxyphenyl)-3-(3-trifluoromethylphenyl)-2-[propenyl]-4-methylene-2-oxo-3-phenyl-1-oxa-3,8-diazaspiro[4,5]decane (E:Z=1.1), m.p.: 124°-126° C.;

8-[3,3-bis(4-fluorophenyl)-2-propenyl]-3-butyl-4-methylene-2-oxo-1-oxa-3,8-diazaspiro[4,5]decane, m.p.: 132.5°-134° C.;

(E)-8-[3-(4-acetyloxyphenyl)-3-(3-trifluoromethylphenyl)-2-propenyl]-3-cyclohexyl-4-methylene-2-oxo-1-oxa-3,8-diazaspiro[4,5]decane, m.p.: 177°-178° C.;

8-[3,3-bis(3,5-dichlorophenyl)-2-propenyl]-3-methyl-4-methylene-2-oxo-1-oxa-3,8-diazaspiro[4,5]decane, m.p.: 141°-143° C.;

(E)-8-[3-(4-acetyloxyphenyl)-3-(3-trifluoromethylphenyl)-2-propenyl]-4-methylene-2-oxo-3-propyl-1-oxa-3,8-diazaspiro[4,5]decane, m.p.: 111°-112° C.;

3-butyl-8-(3,8-diphenyl-2-propenyl)-4-methylene-2-oxo-1-oxa-3,8-diazaspiro[4,5]decane, m.p.: 138°-139° C.;

3-benzyl-8-[4,4-bis(4-fluorophenyl)-3-butenyl]-4-methylene-2-oxo-1-oxa-3,8-diazaspiro[4,5]decane, m.p.: 78°-79° C.;

8-[4,4-bis(4-fluorophenyl)-3-butenyl]-3-tert-butyl-4-methylene-2-oxo-1-oxa-3,8-diazaspiro[4,5]decane, m.p.: 109°-110° C.;

8-[4,4-bis(4-fluorophenyl)-2-propenyl]-3-methyl-4-methylene-2-oxo-1-oxa-3,8-diazaspiro[4,5]decane, m.p.: 141°-142° C.;

8-[4,4-bis(4-fluorophenyl)-3-butenyl]-4-methylene-2-oxo-3-propyl-1-oxa-3,8-diazaspiro[4,5]decane, m.p.: 130°-131° C.;

8-[4,4-bis(4-chlorophenyl)-3-butenyl]-3-methyl-4-methylene-2-oxo-1-oxa-3,8-diazaspiro[4,5]decane, m.p.: 136°-137° C.; and 3-benzyl-8-[4,4-bis(4-chlorophenyl)-3-butenyl]-4-methylene-2-oxo-1-oxa-3,8-diazaspiro[4,5]decane, m.p.: 138°-139° C.

The compounds of the Formula (I) where one of $R^1$ and $R^2$ is hydroxyl while the other is methyl may be connected to a compound of the Formula (IX)

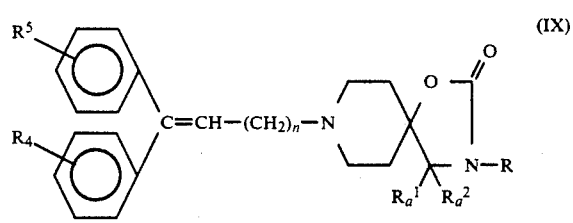

wherein one of $R^1_a$ and $R^2_a$ stands foe a hydroxyl group whereas the other means a methyl group; by reaction with a compound of the Formula (VIII).

The compounds of the Formula (IX) are useful to treat amnesia and memory damage due to hypoxia. The following examples prepare compounds of the Formula (IX):

EXAMPLE 40

Preparation of 8-[3,3-bis(4-fluorophenyl)-2-propenyl]-4-hydroxy-4-methyl-2-oxo-3-n-propyl-1-oxa-3,8-diazaspiro[4,5]decane 9.3 g of 3,3-bis(4-fluorophenyl)-2-propenyl bromide dissolved in 50 ml of acetone are portionwise added to a mixture containing 6.85 g of 4-hydroxy-4-methyl-2-oxo-3-n-propyl-1-oxa-3,8-diazaspiro[4,5]decane and 4.2 g of anhydrous potassium carbonate in 68 ml of anhydrous acetone at room temperature during 1 hour while stirring, then the reaction mixture is stirred at room temperature for an additional 1 hour. After filtering off the inorganic salts and evaporating the solvent under reduced pressure, the residue is taken up in benzene, washed with water, dried over anhydrous sodium sulfate and then the solution is evaporated to its tenth volume under reduced pressure. The product is precipitated by adding n-hexane to the evaporation residue. The crystals are filtered off and dried to give the title compound in 86% yield, m.p.: 128°-129° C.

Analysis: Calculated for $C_{26}H_{30}F_2N_2O_3$ C 68.40; H 6.62; F 8.32; N 6.14%; found: C 68.44; H 6.79; F 8.50; N 6.12%.

The hydrochloride salt is precipitated by adding ethereal hydrogen chloride solution to an ethereal solution of the base, m.p.: 233°-235° C.

The following compounds can analogously be prepared by using the appropriate starting substances.

8-(3,3-diphenyl-2-propenyl)-4-hydroxy-3-isopropyl-4-methyl-2-oxo-1-oxa-3,8-diazaspiro[4,5]decane hydrochloride, m.p.: 219°-221° C.;

8-[3,3-bis(4-fluorophenyl)-2-propenyl]-4-hydroxy-3-isopropyl-4-methyl-2-oxo-1-oxa-3,8-diazaspiro[4,5]decane hydrochloride, m.p.: 255°-260° C.;

EXAMPLE 41

Preparation of
8-[4,4-bis(4-chlorophenyl)-3-butenyl]-3-butyl-4-hydroxy-4-methyl-2-oxo-1-oxa-3,8-diazaspiro[4,5]decane hydrochloride A mixture containing 7.27 g of 3-butyl-4-hydroxy-4-methyl-2-oxo-1-oxa-3,8-diazaspiro[4,5]decane, 12.89 g of 4,4-bis(4-chlorophenyl)-3-butenyl bromide, 4.98 g of anhydrous potassium carbonate and 0.6 g of potassium iodide in 73 ml of methyl isobutyl ketone is gently refluxed under argon while stirring for 6 hours. After cooling down, the inorganic salts are filtered off, washed with methyl isobutyl ketone, the filtrate is washed with water to neutral, dried over anhydrous magnesium sulfate and then the solvent is distilled off under reduced pressure. After recrystallizing the evaporation residue from ethanol, the product obtained is dissolved in ether and the hydrochloride is precipitated by adding ethereal hydrogen chloride solution to obtain 79.3% of the title hydrochloride, m.p.: 230°-233° C. (with decomposition).

Analysis of the base: Calculated for $C_{28}H_{34}Cl_2N_2O_3$ C 64.89; H 6.62; Cl 13.70; N 5.41%; found: C 65.04; H 6.66; Cl 13.62; N 5.48%.

The compounds of the Formula (I) maybe converted to compounds of the Formula (X)

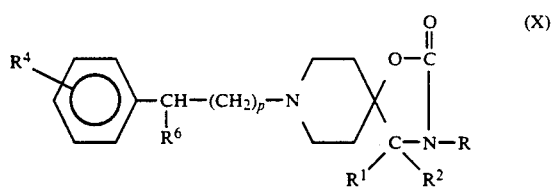

wherein
$R^6$ stands for hydrogen or a phenyl group optionally substituted by one or more halogen(s), one or more $C_{1-4}$alkyl or $C_{1-4}$alkoxy or hydroxyl group(s);
p is 1, 2 or 3.
as well as their acid addition and quaternary ammonium salts and pharmaceutical compositions containing these compounds, by reaction, with a phenylalkane derivative of the formula (XI),

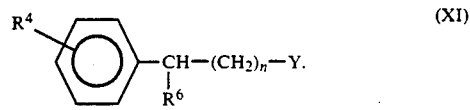

The compounds of the Formula (X) are useful in causing calcium uptake inhibition, and have anti-hypoxic and anti-anoxic activity.

The following examples are directed to preparing the compound of the Formula (X):

EXAMPLE 42

Preparation of
1-oxa-2-oxo-3-propyl-4-methylene-8-[4,4-bis(4-fluorophenyl)butyl]-3,8-diazaspiro[4,5]decane A mixture containing 8.4 g of 1-oxa-2-oxo-3-propyl-4-methylene-3,8-diazaspiro[4,5]decane, 22.4 g of 4,4-bis(4-fluorophenyl)butyl chloride, 16.6 g of anhydrous potassium carbonate and 0.3 g o potassium iodide in 90 ml of methyl isobutyl ketone is boiled under reflux and stirring for 8 hours, then the solvent is distilled off under reduced pressure. After adding benzene and water to the residue, the organic phase is separated, washed with water to neutral, dried over anhydrous magnesium sulfate and evaporated under reduced pressure. The crude product obtained is purified by chromatography on a silica gel column by using ethyl acetate for elution. The eluates are combined, evaporated and the residue is recrystallized from diisopropyl ether to give the title compound in 89% yield, m.p.: 107°-108° C.

Analysis: Calculated for $C_{27}H_{32}F_2N_2O_2$ C 71.34; H 7.10; F 8.36; N 6.16%; found: C 71.50; J 7.23; F 8.28; N 6.07%.

EXAMPLE 43

Preparation of
1-oxa-2-oxo-3-benzyl-4-methylene-8-[2-(4-fluorophenyl)]-3,8-diazaspiro[4,5]decane A mixture containing 10.3 g of 1-oxa-2-oxo-3-benzyl-4-methylene-3,8-diazaspiro[4,5]decane, 16.2 g of 2-(4-fluorophenyl)ethyl bromide and 11.2 ml of triethylamine in 100 ml of methyl isobutyl ketone is refluxed under argon while stirring for 2.5 hours. After cooling down and adding water to the reaction mixture, the organic phase is separated, washed with saturated sodium chloride solution, dried over anhydrous sodium sulfate and evaporated under reduced pressure. The residue is recrystallized under clarifying by activated carbon from hexane and then from diisopropyl ether to obtain the title compound in 31.8% yield, m.p. 100°-101° C.

Analysis: Calculated for $C_{23}H_{25}FN_2O_2$ C 72.61; H 6.62; F 4.99; N 7.36%; found: C 72.8; H 6.54; F 5.22; N 7.53%.

EXAMPLE 44

Preparation of
1-oxa-2-oxo-3-ethyl-4-methylene-8-(3,3-diphenylpropyl)-3,8-diazaspiro[4,5]decane hydrogen maleate A mixture containing 7.9 g of 1-oxa-2-oxo-3-ethyl-3-methylene-3,8-diazaspiro[4,5]decane, 26 g of 3,3-diphenylpropyl-1-tosyloxypropane and 7.4 g of anhydrous sodium carbonate in 100 ml of methyl isopropyl ketone is refluxed under nitrogen while stirring for 5 hours. After evaporating the reaction mixture under reduced pressure, water is added to the residue and extracted with chloroform. The organic phase is washed with water, dried, over anhydrous magnesium sulfate and evaporated under reduced pressure. The crude product is dissolved in acetone and the title salt is precipitated by adding an ethereal solution of maleic acid, m.p.: 168°-170° C.

The base can be liberated from the above salt by adding aqueous sodium hydroxide solution.

Analysis of the base: Calculated for $C_{25}H_{30}N_2O_2$ C 76.89; H 7.74; N 7.17%; found: C 76.95; H 7.89; N 7.24%.

EXAMPLE 45

Preparation of 1-oxa-2-oxo-3-cyclohexyl-4-hydroxy-4-methyl-8-[2-(4-chlorophenyl)ethyl]-3,8-diazaspiro[4,5]decane hydrochloride 10.7 g of 1-oxa-2-oxo-3-cyclohexyl-4-hydroxy-4-methyl-3,8-diazaspiro[4,5]decane are refluxed with 13.2 g of 2-(4-chlorophenyl)ethyl bromide, 8.2 g of anhydrous powdered potassium carbonate and 0.7 g of potassium iodide in 110 ml of methyl isobutyl ketone under nitrogen while stirring for 6 hours. After evaporating the solvent under reduced pressure and adding water to the residue, the mixture is extracted with benzene. The combined benzene solution is washed with water to neutral, dried over anhydrous sodium sulfate, then the benzene solution is filtered through an aluminum oxide layer and evaporated under reduced pressure. After recrystallization of the residue from hexane, the base is converted to the hydrochloride by adding hydrogen chloride in diisopropyl ether solution. Thus, the title hydrochloride is obtained in 58.4% yield with a decomposition point of 310°–315° C.

Analysis of the base: Calculated for $C_{22}H_{31}ClN_2O_3$ C 63.93; H 7.68; Cl 8.71; N 6.88%; found: C 65.10; H 7.53; Cl 8.60; N 7.00%.

By using the appropriate starting substances the following compounds are prepared in an analogous manner as described in Examples 42–45:

1-Oxa-2-oxo-3-methyl-4-methylene-8-(2-phenylethyl)-3,8-diazaspiro[4,5]decane, m.p.: 119°–120° C.;

1-Oxa-2-oxo-4-methylene-3-phenyl-8-[2-(4-chlorophenyl)ethyl]-3,8-diazaspiro[4,5]decane, m.p.: 134°–135° C.;

1-Oxa-2-oxo-3-ethyl-4-methylene-8-[2-(4-methylphenyl)-ethyl]-3,8-diazaspiro[4,5]decane hydrochloride, decomp. at 280°–282° C.;

1-Oxa-2-oxo-3-cyclohexyl-4-methylene-8-[2-(4-fluorophenyl)-ethyl-3,8-diazaspiro[4,5]decane, m.p.: 125°–126° C.;

1-Oxa-2-oxo-4-methylen-3-phenyl-8-[2-(4-fluorophenyl)ethyl]-3,8-diazaspiro[4,5]decane, m.p.: 145°–147° C.;

1-Oxa2-oxo-3-ethyl-4-methylene-8-(2-phenylethyl)-3,8-diazaspiro[4,5]Decane, m.p.: 121°–122° C.;

1-Oxa-2-oxo-3-tert-butyl-4-methylene-8-[4,4-bis(4-fluorophenyl)butyl]-3,8-diazaspiro[4,5]decane, m.p.: 90°–92° C.;

1-Oxa-2-oxo-3-isopropyl-4-methylene-8-[4,4-bis(4-fluorophenyl)butyl]-3,8-diazaspiro[4,5]decane, m.p.: 118°–119° C.;

1-Oxa-2-oxo-3-methyl-4-methylene-8-[4,4-bis(4-fluorophenyl)butyl]-3,8-diazaspiro[4,5]decane, m.p.: 90°–91° C.;

1-Oxa-2-oxo-3-tert-butyl-4-methylene-8-(2-phenylethyl)3,8-diazaspiro[4,5]decane, m.p.: 106°–107° C.;

1-Oxa-2-oxo-3-isopropyl-4-methylene-8-[2, (4-chlorophenyl)-ethyl]-3,8-diazaspiro[4,5]decane, m.p.: 101°–102° C.;

1-Oxa-2-oxo-3-methyl-4-methylene-8-[2, (4-fluorophenyl)ethyl]-3,8-diazaspiro[4,5]decane, m.p.: 74°–75° C.;

1-Oxa-2-oxo-3-ethyl-4-methylene-8-[,4,4-bis(4-fluorophenyl)-butyl]-3,8-diazaspiro[4.5]decane, m.p.: 111°–112° C.;

1-Oxa-2-oxo-3-isopropyl-4-methylene-8-[2-(4-fluorophenyl)-ethyl]-3,8-diazaspiro[4,5]decane, m.p.: 103°–104° C.;

1-Oxa-2-oxo-4-methylene-3-phenyl-8-[4,4-bis(4-fluorophenyl)butyl]-3,8-diazaspiro[4,5]decane, m.p.: 125°–126° C.;

1-Oxa-2-oxo-4-methylene-3-propyl-8-[2-(4-fluorophenyl)ethyl]-3,8-diazaspiro[4,5]decane, m.p.: 78°–79° C.;

1-Oxa-2-oxo-3-[2-(3,4-dimethoxyphenyl)ethyl]-4-methylene-8-(2-phenylethyl)-3,8-diazaspiro[4,5]decane, m.p.: 114°–115° C.;

1-Oxa-2-oxo-3-benzyl-4-methylene-8-[4,4-bis(4-fluorophenyl)butyl]-3,8-diazaspiro[4,5]decane, m.p.: 81°–82° C.;

1-Oxa-2-oxo-3-decyl-4-methylene-8-[4,4-bis(4-fluorophenyl)butyl]-3,8-diazaspiro[4,5]decane hydrogen maleate, m.p.: 106°–107° C.;

1-Oxa-2-oxo-3-cyclohexyl-4-methylene-8-[4,4-bis(4-fluorophenyl)butyl]-3,8-diazaspiro[4,5]decane, m.p.: 121°–122° C.;

1-Oxa-2-oxo-3-butyl-4-methylene-8-(2-phenylethyl)-3,8-diazaspiro[4,5]decane, m.p.: 70°–71° C.;

1-Oxa-2-oxo-3-methyl-4-methylene-8-[2-(4-chlorophenyl)-ethyl]-3,8-diazaspiro[4,5]decane, m.p.: 118°–119° C.;

1-Oxa-2-oxo-3-tert-butyl-4-methylene-8-[2-(4-chlorophenyl)ethyl]-3,8-diazaspiro[4,5]decane, m.p.: 104°–105° C.;

1-Oxa-2-oxo-3-ethyl-4-methylene-8-[2-(4-fluorophenylethyl]-3,8-diazaspiro[4,5]decane, m.p.: 83°–84° C.;

1-Oxa-2-oxo-3-methyl-4-methylene-8-[2-(3,4-dimethoxyphenyl)ethyl]-3,8-diazaspiro[4,5]decane hydrochloride, m.p.: 278°–280° C.; and 1-Oxa-2-oxo-3-tert-butyl-4-methylene-8-[2-(4-fluorophenyl)-ethyl]-3,8-diazaspiro[4,5]decane, m.p.: 93°–94° C.

The compounds of the Formula (I) may also be connected to compounds of the Formula (XII)

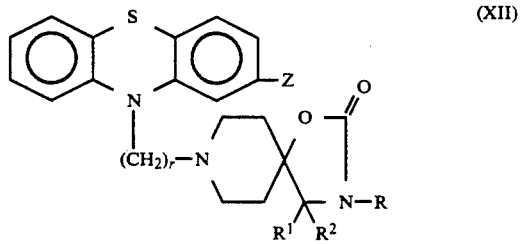

(XII)

wherein

Z stands for hydrogen, halogen, trihalomethyl or a $C_{2-4}$alkanoyl group; and r is 2 or 3, as well as their acid addition and quaternary ammonium salts, by reaction with a phenothiazine derivative of the formula (XIII),

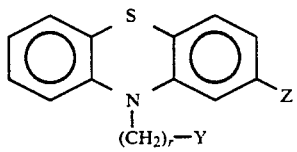

(XIII)

having anti-allergy and antipsychotic activity.

The following examples are directed to preparing compounds of the Formula (XII).

EXAMPLE 46

Preparation of 3-methyl-4-methylene-2-oxo-8-[3-(2-trifluoromethyl-10H-phenothiazin-10yl)propyl]-1-oxa,3,8-diazaspiro[4,5]decane A mixture containing 11.0 g of 3-methyl-4-methylene-2-oxo-1-oxa-3,8-diazaspiro[4,5]decane, 41.3 g of 3-(2-trifluoromethyl-10H-phenothiazin-10yl)propyl chloride, 16.6 g of anhydrous potassium carbonate and 0.6 g of potassium iodide in 110 ml of methyl isobutyl ketone is refluxed under nitrogen while stirring for 6 hours. After evaporating the solvent under reduced pressure benzene and water are added to the evaporation residue, the organic phase is separated, washed with water to neutral, dried over anhydrous sodium sulfate, then the solution is evaporated under reduced pressure. The solid residue is boiled with hexane, after cooling down the precipitate is filtered off and recrystallized from ethanol to give the title compound in a yield of 75.3%; m.p.: 116°-117.5° C.

Analysis:
Calculated for $C_{25}H_{26}F_3O_2S$
C 61.33; H 5.35; F 11.64; N 8.58 S 6.55%;
found: C 61.50; H 5.38; F 11.38 N 8.34 S 6.34%.

EXAMPLE 47

Preparation of 8-[3-(2-acetyl-10H-phenothiazin-10-yl)propyl-3-methyl-4-methylene-2-oxo-1-oxa-3,8-diazaspiro[4,5]decane A mixture containing 7.3 g of 3-methyl-4-methylene-2-oxo-1-oxa-3,8-diazaspiro[4,5]decane, 9 ml of anhydrous triethylamine, 22.0 g of 3-(2-acetyl-10H-phenothiazin-10yl)-propyl bromide and 80 ml of methyl isobutyl ketone is refluxed under argon while stirring for 6 hours. After cooling down the organic phase is washed with water, dried over anhydrous magnesium sulfate and evaporated under reduced pressure. The crude product obtained is purified by chromatography on a silica gel column by using first chloroform and then ethyl acetate as eluating agent. After combining the ethyl acetate eluate is evaporated under reduced pressure and the residue is recrystallized from ethanol to give the title compound in 84.5% yield, m.p.: 105°-106° C.

Analysis: Calculated for $C_{26}H_{29}N_3O_3S$ C 67.36; H 6.30; N 9.06; S 6.92%; found: C 67.48; H 6.51; N 9.01 S 7.11%.

By using the appropriate starting substances the following substances are prepared in an analogous way as described in Examples 46, or 47 in Example 48 to be described hereinafter.

8-3-(2-Acetyl-10H-phenothiazin-10-yl)propyl]-3,4-dimethyl-4-hydroxy-2-oxo-1-oxa-3,8-diazaspiro[4,5]decane hydrochloride, m.p.: 165°-168° C. (with decomposition);

8-[3-(2-Chloro-10H-phenothiazin-10-yl)propyl]-3-methyl-4-methylene-2-oxo-1-oxa-3,8-diazaspiro[4,5decane, m.p.: 142°-143° C.;

4-Methylene-2-oxo-8-[3-(10H-phenothiazin-10-yl)propyl]-3-n-propyl-1-oxa-3,8-diazaspiro[4,5]decane, m.p.: 98°-99° C.;

3-Cyclohexyl-4-methylene-2-oxo-8-[3-(10H-phenothiazin-10-yl)propyl]-1-oxa-3,8-diazaspiro[4,5]decane, m.p.: 159°-160° C.;

4-Methylene-2-oxo-8-[3-(10H-phenothiazin-10-yl)propyl]-2-oxo-3-tert-butyl-1-oxa-3,8-diazaspiro[4,5 decane, m.p.; 96°-97° C.;

8-[3-(2-Chloro-10H-phenothiazin-10yl)propyl]-3-isopropyl-4-methylene-2-oxo-1-oxa-3,8-diazaspiro[4,5]-decane, m.p.: 162°-163° C.;

4-Methylene-2-oxo-3-propyl-8-[3-(2-trifluoromethyl-10H-phenothiazin-10-yl)propyl]-1-oxa-3,8-diazaspiro[4,5]decane, m.p. 119°-121° C.;

8-[3-(2-Acetyl-10H-phenothiazin-10-yl)propyl]-3-n-decyl-4-methylene-2-oxo-1-oxa-3,8-diazaspiro[4,5]-decane hydrogen maleate, m.p.: 108°-110° C. (with decomposition);

3-Methyl-4-methylene-2-oxo-8-[3-(10H-phenothiazin-10-yl)propyl]-1-oxo-3,8-diazasopiro[4,5]decane, m.p.: 132°-133° C. obtained by reacting 3-methyl-4-methylene-2-oxo-1-oxa-3,8-diazaspiro[4,5]decane with 3-(10-phenothiazin-10-yl)propyl p-toluene-sulfonate;

8-[3-(2-Chloro-10H-phenothiazin-10-yl)propyl]-3-n-butyl-4-methylene-2-oxo-1-oxa-3,8-diazaspiro[4,5]-decane, m.p.: 100°-101° C.;

8-[3(2-Chloro-10H-phenothiazin-10-yl)propyl]-3-cyclohexyl-4-methylene-2-oxo-1-oxa-3,8-diazaspiro[4,5]decane, m.p.: 177°-178° C.;

8-[3-(2-Chloro-10H-phenothiazin-10-yl)propyl]-3-ethyl-4-hydroxy-4-methyl-2-oxo-1-oxa,3,8diazaspiro[4,5]-decane, m.p.: 155°-156° C.; the hydrochloride decomposes at 220°-222° C.;

8-[3-(2-Chloro-10H-phenothiazin10-yl)propyl]-4-methylene-2-oxo-3-n-propyl-1-oxa-3,8-diazaspiro[4,5]decane, m.p.: 118°-119° C.;

3-Ethyl-4-methylene-2-oxo-8-[-3-(2-trifluoromethyl-10H-phenothiazin-10-yl)propyl]-1-oxa,3,8-diazaspiro[4,5]decane, m.p. 117°-119° C.;

3n-Butyl-4-methylene-2-oxo-8-[3-(2-trifluoromethyl-10H-phenothiaizin-10-yl)propyl]-1-oxa-3,8-diazaspiro[4,5]decane, m.p. 104°-105° C.;

4-Methylene-2-oxo-3-tert-butyl-8-[3-(2-trifluoromethyl-10H-phenothiazin-10-yl)propyl]-1-oxa-3,8-diazaspiro[4,5]decane, m.p. 129°-130° C.; and 8-2-(2-Chloro-10H-phenothiazin-10-yl)ethyl]-3-n-butyl-4-methylene-2-oxo-1-oxa-3,8-diazaspiro[4,5]decane, m.p.: 108°-110° C.

EXAMPLE 48

Preparation of 3-ethyl-4-methylene-2-oxo-8-[3-(10H-phenothiazin-10-yl)propyl]-1-oxa-3,8-diazaspiro[4,5]decane 0.6 g of sodium hydride (60% oily dispersion) is added to a solution of 3.0 g of phenothiazine in 20 ml of anhydrous dimethylformamide under argon, then the reaction mixture is stirred at 50° to 60° C. for 2 hours. Thereafter, 3.9 g of 8-(3-chloropropyl)-3-ethyl-4-methylene-2-oxo-1oxa-3,8-diazaspiro]4,5]decane dissolved in 20 ml of dimethylformamide are dropwise added and the mixture is stirred at 40° to 50° C. for additional 6 to 7 hours. After cooling down saturated ammonium chloride solution is added to the reaction mixture under argon and the solvent is evaporated under reduced pressure. After taking up the evaporation residue in benzene and washing the benzene solution with water the solution is dried over anhydrous sodium sulfate and then evaporated under reduced pressure. The residue is recrystallized from ethanol to give the title product in 57.6% yield, m.p.: 122°–123° C.

Analysis: Calculated for $C_{25}H_{29}N_3O_2$ C 68.93; H 6.71; N 9.65; S 7.36% found: C 62.08; H 6.77; N 9.78 S 7.23%.

We claim:

1. A compound of the formula (I),

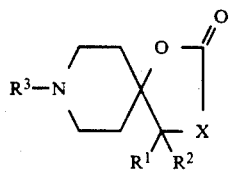

wherein

X means oxygen or an >NR group, wherein R stands for hydrogen; a $C_{1-12}$ alkyl; $C_{3-6}$cycloalkyl; carbocyclic $C_{6-10}$ aryl or carbocyclic $C_{6-10}$ aryl-$C_{1-4}$alkyl group, the two latter substituents are optionally substituted on their aromatic moiety by one or more, same or different halogens, one or more $C_{1-4}$alkyl, $C_{1-4}$alkoxy or trihalomethyl group; or a tosyl group;

$R^1$ and $R^2$ together represent a methylene group or, when X stands for an >NR group, one of $R^1$ and $R^2$ may represent a hydroxyl group and the other one is a methyl group; and $R^3$ means hydrogen, benzyl, ($C_{1-4}$alkoxy) carbonyl, phenoxycarbonyl, formyl, piperidine-1-ylcarbonyl, morpholin-4-ylcarbonyl, 4-methylpiperazin-1-ylcarbonyl, 4-(2-hydroxyethyl)piperazin-1-ylcarbonyl, 2-chloro-3-nicotinoylcarbamoyl or $C_{1-6}$alkylcarbamoyl group, as well as their acid addition and quaternary ammonium salts.

2. A compound defined in claim 1 and selected from the group consisting of 3-methyl-4-methylene-2-oxo-1-oxa-3,8-diazaspiro[4,5]decane, 3-ethyl-4-methylene-2-oxo-1-oxa-3,8-diazaspiro[4,5]decane, 3-cyclohexyl-4-methylene-2-oxo-1-oxa-3,8-diazaspiro[4,5]-decane, 4-methylene-2-oxo-3-propyl-1-oxa-3,8-diazaspiro[4,5]decane, 3-isopropyl-4-methylene-2-oxo-1oxa-3,8-diazaspiro[4,5]decane, 3-butyl-4-methylene-2-oxo-1-oxa-3,8-diazaspiro[4,5]-decane, 3-tert-butyl-4-methylene-2-oxo-1oxa-3,8-diazaspiro[4,5]decane, 3-heptyl-4-methylene-2-oxo-1-oxa-3,8-diazaspiro[4,5]decane, 4-methylene-2-oxo-3-phenyl-1-oxa,-3,8-diazaspiro[4,5]decane, 3-decyl-4methylene-2-oxo-1-oxa-3,8-diazaspiro[4,5]-decane, 3-benzyl-4-methylene-2-oxo-1-oxa-3,8-diazaspiro[4,5]decane, 3-[2-(3,4-dimethoxyphenyl)ethyl]-4-methylene-2-oxo-1-oxa-3,8-diazaspiro[4,5]decane, 4-hydroxy-4-methyl-2-oxo-1-oxa-3,8-diazaspiro[4,5]-decane, 3,4-dimethyl-4-hydroxy-2-oxo-1-oxa-3,8-diazaspiro[4,5]decane, 3-[2(3,4-dimethoxyphenyl)ethyl]-4-hydroxy-4methyl-2-oxo-1-oxa-3,8diazaspiro[4,5]decane, 3-decyl-4hydroxy-3-methyl-2-oxo-1oxa-3,8diazaspiro[4,5]-decane, 3-heptyl-4-hydroxy-4-methyl-2-oxo-1-oxa-3,8-diazaspiro[4,5]-decane, 8-benzyl-4-methylene-2-oxo-1,3-dioxa-8-diazaspiro[4,5]decane, 4-methylene-3-(1-naphthyl)-2-oxo-1-oxa-3,8-diazaspiro[4,5]-decane, as well as the acid addition and quaternary ammonium salts of these compounds.

3. 3-tert-butyl-4-methylene-2-oxo-1-oxa-3,8-diazaspiro[4,5]decane or a pharmaceutically acceptable acid addition or quaternary ammonium salt thereof as defined in claim 1.

4. The compound of the Formula (I) defined in claim 1 wherein X is an >NR group and $R^3$ is hydrogen, or a pharmaceutically acceptable acid addition or quaternary ammonium salt thereof.

* * * * *